US006369201B1

(12) United States Patent
Barker et al.

(10) Patent No.: US 6,369,201 B1
(45) Date of Patent: Apr. 9, 2002

(54) MYOSTATIN MULTIMERS

(75) Inventors: Christopher A. Barker, Saskatoon (CA); Mohamad Morsey, Niantic, CT (US)

(73) Assignee: MetaMorphix International, Inc., Baltimore, MD (US)

( * ) Notice: Subject to any disclaimer, the term of this patent is extended or adjusted under 35 U.S.C. 154(b) by 0 days.

(21) Appl. No.: 09/252,149

(22) Filed: Feb. 18, 1999

Related U.S. Application Data

(60) Provisional application No. 60/075,213, filed on Feb. 19, 1998.

(51) Int. Cl.$^7$ ...................... C07K 16/22; C07K 14/476; C07K 16/46; C12N 15/63
(52) U.S. Cl. ................. 530/387.1; 530/387.1; 530/350; 530/351; 530/399; 435/69.7; 435/320.1
(58) Field of Search ................................. 435/7.1, 69.1, 435/69.7, 320.1; 530/387.1, 387.9, 350, 399, 351

(56) References Cited

U.S. PATENT DOCUMENTS

| 5,827,733 A | 10/1998 | Lee et al. | 435/325 |
| 5,914,234 A | 6/1999 | Lee et al. | 435/7.1 |
| 5,994,618 A | 11/1999 | Lee et al. | 800/18 |

FOREIGN PATENT DOCUMENTS

| WO | WO 94/21681 | 9/1994 | 530/399 |
| WO | WO 96/01845 | 1/1996 | 530/350 |
| WO | WO 98/33887 | 8/1998 | 800/2 |
| WO | WO 99/02667 | 1/1999 | 800/2 |
| WO | WO 99/06559 | 2/1999 | 435/325 |
| WO | WO 99/24618 | 5/1999 | 435/6 |
| WO | WO 99/40181 | 8/1999 | 800/3 |
| WO | WO 01/05820 | 1/2001 | |

OTHER PUBLICATIONS

Immunology A Short Course. Benjamini and Leskowitz Wiley–Liss,Inc. Second Edition, Copyright 1991.*
Casas et al., "Association of the Double–Muscling Locus on Bovine Chromosome Two (BTA2) With Carcass Traits," *J. Anim. Sci.* 75(1):147 (1997).
Dickman, Steven, "Gene Mutation Provides More Meat on the Hoof," *Science* 277:1922–1923 (1977).
Gonzalez–Cadavid et al., "Organization of the Human Myostatin Gene and Expression in Healthy Men and HIV–infected Men With Muscle Wasting," *Proc. Natl. Acad. Sci. USA* 95:14938–14943 (1998).
Grobet et al., "A Deletion in the Bovine Myostatin Gene Causes the Double–Muscled Phenotype in Cattle," *Nature Genetics* 17:71–74 (1997).
Kambadur et al., "Mutations in Myostatin (GDF8) in Double–Muscled Belgian Blue and Piedmontese Cattle," *Genome Research* 7:910–916 (1997).
McKnight, Steven L., "Gatekeepers of Organ Growth," *Proc. Natl. Acad. Sci. USA* 94:12249–12250 (1997).
McPherron et al., "Double Muscling in Cattle Due to Mutations in the Myostatin Gene," *Proc. Natl. Acad. Sci. USA* 94:12457–12461 (1997).
McPherron et al., "Regulation of Skeletal Muscle Mass in Mice by a New TGF–β Superfamily Member," *Nature* 387:83–90 (1997).
Ménnissier, F., "Present State of Knowledge About the Genetic Determination of Muscular Hypertrophy or the Double Muscled Trait in Cattle," *Muscle Hypertrophy of Genetic Origin . . .* :387–428 (1982).
Shahin et al., "Growth Patterns of Muscle, Fat and Bone, and Carcass Composition of Double Muscled and Normal Cattle," *Can. J. Anim. Sci.* 65(2):279–294 (1985).
Westhusin, Mark, "From Mighty Mice to Mighty Cows," *Nature Genetics* 17:4–5 (1997).

* cited by examiner

Primary Examiner—Elizabeth Kemmerer
Assistant Examiner—Regina M. DeBerry
(74) Attorney, Agent, or Firm—Robins & Pasternak LLP

(57) ABSTRACT

Immunological compositions and methods for reducing myostatin activity in vertebrate subjects are disclosed. The compositions include myostatin peptide immunogens, myostatin multimers and or myostatin immunoconjugates capable of eliciting an immune response in a vertebrate subject to which the compositions are administered. The methods are useful for the treatment of a wide variety of disorders.

28 Claims, 17 Drawing Sheets

| | | |
|---|---|---|
| 1 MMQKLQMYVY 10 | 11 IYLFMLIAAG 20 | 21 PV-----DLNEGSER 30 Mouse |
| 1 M I QKPQMYVY 10 | 11 IYLFVLI AAG 20 | 21 PV-----DLNEDSER 30 Rat |
| 1 -M QKLQ L CVY 9 | 10 IYLFMLI VAG 19 | 20 PV-----DLNENSEQ 29 Human |
| 1 -M QKLQ L CVY 9 | 10 IYLFMLI VAG 19 | 20 PV-----DLNENSEQ 29 Baboon |
| 1 -M QKLQ I SVY 9 | 10 IYLFMLI VAG 19 | 20 PV-----DLNENSEQ 29 Bovine |
| 1 -M QKLQ I YVY 9 | 10 IYLFMLI VAG 19 | 20 PV-----DLNENSEQ 29 Porcine |
| 1 -M QKLQ I FVY 9 | 10 IYLFMLLVAG 19 | 20 PV-----DLNENSEQ 29 Ovine |
| 1 -M QKLA VYVY 9 | 10 IYLFMQI AVD 19 | 20 PV-----ALDGSSQP 29 Chicken |
| 1 -M Q I LA VYVY 9 | 10 IYLFMQ I LVH 19 | 20 PV-----ALDGSSQP 29 Turkey |
| 1 -MH FTQ-----VL 7 | 8  ISLS VL I ACG 17 | 18 PVGYGDITAHQQP 30 Zebrafish |
| | | |
| 31 EENVEKEGLC 40 | 41 NACA WRQNTR 50 | 51 YS  RI E AIKIQ 60 Mouse |
| 31 EANVEKEGLC 40 | 41 NACA WRQNTR 50 | 51 YS  RI E AIKIQ 60 Rat |
| 30 KENVEKEGLC 39 | 40 NACT WRQNTK 49 | 50 SS  RI E AIKIQ 59 Human |
| 30 KENVEKEGLC 39 | 40 NACT WRQNTK 49 | 50 SS  RI E AIKIQ 59 Baboon |
| 30 KENVEKEGLC 39 | 40 NACL WRE NTT 49 | 50 SS  RLE AIKIQ 59 Bovine |
| 30 KENVEKEGLC 39 | 40 NACMWRQNTK 49 | 50 SS  RLE AIKIQ 59 Porcine |
| 30 KENVEKKGLC 39 | 40 NACL WRQNNK 49 | 50 SS  RLE AIKIQ 59 Ovine |
| 30 TENAEKDGLC 39 | 40 NACT WRQNTK 49 | 50 SS  RI E AIKIQ 59 Chicken |
| 30 TENAEKDGLC 39 | 40 NACT WRQNTK 49 | 50 SS  RI E AIKIQ 59 Turkey |
| 31 STAT EES ELC 40 | 41 S TCE FRQHSK 50 | 51 LM RLHAIKSQ 60 Zebrafish |
| | | |
| 61 ILSKLRLETA 70 | 71 PNISKDA IRQ 80 | 81 LLPRAPPLRE 90 Mouse |
| 61 ILSKLRLETA 70 | 71 PNISKDA IRQ 80 | 81 LLPRAPPLRE 90 Rat |
| 60 ILSKLRLETA 69 | 70 PNISKDV IRQ 79 | 80 LLPKAPPLRE 89 Human |
| 60 ILSKLRLETA 69 | 70 PNISKDA IRQ 79 | 80 LLPKAPPLRE 89 Baboon |
| 60 ILSKLRLETA 69 | 70 PNISKDA IRQ 79 | 80 LLPRAPPLLE 89 Bovine |
| 60 ILSKLRLETA 69 | 70 PNISKDA IRQ 79 | 80 LLPRAPPLRE 89 Porcine |
| 60 ILSKLRLETA 69 | 70 PNISKDA IRQ 79 | 80 LLPRAPPLRE 89 Ovine |
| 60 ILSKLRLEQA 69 | 70 PNISRDV IKQ 79 | 80 LLPRAPPLQE 89 Chicken |
| 60 ILSKLRLEQA 69 | 70 PNISRDV IKQ 79 | 80 LLPRAPPLQE 89 Turkey |
| 61 ILSKLRLKQA 70 | 71 PNISRDVVKQ 80 | 81 LLPRAPPLQQ 90 Zebrafish |
| | | |
| 91 LI DQYDVQRD 100 | 101 DS SDGSLEDD 110 | 111 DYH ATTET I I 120 Mouse |
| 91 LI DQYDVQRD 100 | 101 DS SDGSLEDD 110 | 111 DYH ATTET I I 120 Rat |
| 90 LI DQYDVQRD 99 | 100 DS SDGSLEDD 109 | 110 DYH ATTET I I 119 Human |
| 90 LI DQYDVQRD 99 | 100 DS SDGSLEDD 109 | 110 DYH ATTET I I 119 Baboon |
| 90 LI DQFDVQRD 99 | 100 AS SDGSLEDD 109 | 110 DYH ARTETV I 119 Bovine |
| 90 LI DQYDVQRD 99 | 100 DS SDGSLEDD 109 | 110 DYH ATTET I I 119 Porcine |
| 90 LI DQYDVQRD 99 | 100 DS SDGSLEDD 109 | 110 DYH VTTETV I 119 Ovine |
| 90 LI DQYDVQRD 99 | 100 DS SDGSLEDD 109 | 110 DYH ATTET I I 119 Chicken |
| 90 LI DQYDVQRD 99 | 100 DS SDGSLEDD 109 | 110 DYH ATTET I I 119 Turkey |
| 91 LLDQYDVLGD 100 | 101 DSKDGAVEED 110 | 111 DEH ATTET IM 120 Zebrafish |

FIG. 1A

| | | | |
|---|---|---|---|
| 121 TMPTESDFLM 130 | 131 QADGKPKCCF 140 | 141 FKFSSKIQYN 150 | Mouse |
| 121 TMPTESDFLM 130 | 131 QADGKPKCCF 140 | 141 FKFSSKIQYN 150 | Rat |
| 120 TMPTESDFLM 129 | 130 QVDGKPKCCF 139 | 140 FKFSSKIQYN 149 | Human |
| 120 TMPTESDFLM 129 | 130 QVDGKPKCCF 139 | 140 FKFSSKIQYN 149 | Baboon |
| 120 TMPTESDLL T 129 | 130 QVEGKPKCCF 139 | 140 FKFSSKIQYN 149 | Bovine |
| 120 TMPTESDLLM 129 | 130 QVEGKPKCCF 139 | 140 FKFSSKIQYN 149 | Porcine |
| 120 TMPTESDLL A 129 | 130 EVQEKPKCCF 139 | 140 FKFSSKIQHN 149 | Ovine |
| 120 TMPTESDFL V 129 | 130 QMEGKPKCCF 139 | 140 FKFSSKIQYN 149 | Chicken |
| 120 TMPTESDFL V 129 | 130 QMEGKPKCCF 139 | 140 FKFSSKIQYN 149 | Turkey |
| 121 TMATEPDPI V 130 | 131 QVDRKPKCCF 140 | 141 FS FSPKIQAN 150 | Zebrafish |
| | | | |
| 151 KVVKAQLW IY 160 | 161 LRP VKTPTTV 170 | 171 FVQILRLIKP 180 | Mouse |
| 151 KVVKAQLW IY 160 | 161 LRAVKTPTTV 170 | 171 FVQILRLIKP 180 | Rat |
| 150 KVVKAQLW IY 159 | 160 LRP VETPTTV 169 | 170 FVQILRLIKP 179 | Human |
| 150 KVVKAQLW IY 159 | 160 LRP VETPTTV 169 | 170 FVQILRLIKP 179 | Baboon |
| 150 KLVKAQLW IY 159 | 160 LRP VKTPATV 169 | 170 FVQILRLIKP 179 | Bovine |
| 150 KVVKAQLW IY 159 | 160 LRP VKTPTTV 169 | 170 FVQILRLIKP 179 | Porcine |
| 150 KVVKAQLW IY 159 | 160 LRP VKTPTTV 169 | 170 FVQILRLIKP 179 | Ovine |
| 150 KVVKAQLW IY 159 | 160 LRQVQKPTTV 169 | 170 FVQILRLIKP 179 | Chicken |
| 150 KVVKAQLW IY 159 | 160 LRQVQKPTTV 169 | 170 FVQILRLIKP 179 | Turkey |
| 151 R I VRAQLWVH 160 | 161 LRP AEEATTV 169 | 170 FLQISRLM-P 179 | Zebrafish |
| | | | |
| 181 MKDGTRYTGI 190 | 191 RSLKLDMSPG 200 | 201 TGIWQSIDVK 210 | Mouse |
| 181 MKDGTRYTGI 190 | 191 RSLKLDMSPG 200 | 201 TGIWQSIDVK 210 | Rat |
| 180 MKDGTRYTGI 189 | 190 RSLKLDMNPG 199 | 200 TGIWQSIDVK 209 | Human |
| 180 MKDGTRYTGI 189 | 190 RSLKLDMNPG 199 | 200 TGIWQSIDVK 209 | Baboon |
| 180 MKDGTRYTGI 189 | 190 RSLKLDMNPG 199 | 200 TGIWQSIDVK 209 | Bovine |
| 180 MKDGTRYTGI 189 | 190 RSLKLDMNPG 199 | 200 TGIWQSIDVK 209 | Porcine |
| 180 MKDGTRYTGI 189 | 190 RSLKLDMNPG 199 | 200 TGIWQSIDVK 209 | Ovine |
| 180 MKDGTRYTGI 189 | 190 RSLKLDMNPG 199 | 200 TGIWQSIDVK 209 | Chicken |
| 180 MKDGTRYTGI 189 | 190 RSLKLDMNPG 199 | 200 TGIWQSIDVK 209 | Turkey |
| 180 V KDGGRHR-I 188 | 189 RSLK IDV NAG 198 | 199 VTSWQSIDVK 208 | Zebrafish |
| | | | |
| 211 TVLQNWLKQP 220 | 221 ESNLGIEIKA 230 | 231 LD ENGHDLAV 240 | Mouse |
| 211 TVLQNWLKQP 220 | 221 ESNLGIEIKA 230 | 231 LD ENGHDLAV 240 | Rat |
| 210 TVLQNWLKQP 219 | 220 ESNLGIEIKA 229 | 230 LD ENGHDLAV 239 | Human |
| 210 TVLQNWLKQP 219 | 220 ESNLGIEIKA 229 | 230 LD ENGHDLAV 239 | Baboon |
| 210 TVLQNWLKQP 219 | 220 ESNLGIEIKA 229 | 230 LD ENGHDLAV 239 | Bovine |
| 210 TVLQNWLKQP 219 | 220 ESNLGIEIKA 229 | 230 LD ENGHDLAV 239 | Porcine |
| 210 TVLQNWLKQP 219 | 220 ESNLGIEIKA 229 | 230 LD ENGHDLAV 239 | Ovine |
| 210 TVLQNWLKQP 219 | 220 ESNLGIEIKA 229 | 230 FD ETGRDLAV 239 | Chicken |
| 210 TVLQNWLKQP 219 | 220 ESNLGIEIKA 229 | 230 FD ENGRDLAV 239 | Turkey |
| 209 QVLTVWLKQP 218 | 219 ETNRGIEINA 228 | 229 YDAKGNDLAV 238 | Zebrafish |

FIG. 1B

| | | | |
|---|---|---|---|
| 241 TFPGPGEDGL 250 | 251 NPFLEVKVTD 260 | 261 TPKRSRRDFG 270 | Mouse |
| 241 TFPGPGEDGL 250 | 251 NPFLEVKVTD 260 | 261 TPKRSRRDFG 270 | Rat |
| 240 TFPGPGEDGL 249 | 250 NPFLEVKVTD 259 | 260 TPKRSRRDFG 269 | Human |
| 240 TFPGPGEDGL 249 | 250 NPFLEVKVTD 259 | 260 TPKRSRRDFG 269 | Baboon |
| 240 TFPEPGEDGL 249 | 250 TPFLEVKVTD 259 | 260 TPKRSRRDFG 269 | Bovine |
| 240 TFPGPGEDGL 249 | 250 NPFLEVKVTD 259 | 260 TPKRSRRDFG 269 | Porcine |
| 240 TFPEPGEEGL 249 | 250 NPFLEVKVTD 259 | 260 TPKRSRRDFG 269 | Ovine |
| 240 TFPGPGEDGL 249 | 250 NPFLEVRVTD 259 | 260 TPKRSRRDFG 269 | Chicken |
| 240 TFPGPGEDGL 249 | 250 NPFLEVRVTD 259 | 260 TPKRSRRDFG 269 | Turkey |
| 239 TSTETGEDGL 248 | 249 LPFMEVKI SE 258 | 259 GPKRIRRDSG 268 | Zebrafish |
| | | | |
| 271 LDCDEHSTES 280 | 281 RCCRYPLTVD 290 | 291 FEAFGWDWII 300 | Mouse |
| 271 LDCDEHSTES 280 | 281 RCCRYPLTVD 290 | 291 FEAFGWDWII 300 | Rat |
| 270 LDCDEHSTES 279 | 280 RCCRYPLTVD 289 | 290 FEAFGWDWII 299 | Human |
| 270 LDCDEHSTES 279 | 280 RCCRYPLTVD 289 | 290 FEALGWDWII 299 | Baboon |
| 270 LDCDEHSTES 279 | 280 RCCRYPLTVD 289 | 290 FEAFGWDWII 299 | Bovine |
| 270 LDCDEHSTES 279 | 280 RCCRYPLTVD 289 | 290 FEAFGWDWII 299 | Porcine |
| 270 LDCDEHSTES 279 | 280 RCCRYPLTVD 289 | 290 FEAFGWDWII 299 | Ovine |
| 270 LDCDEHSTES 279 | 280 RCCRYPLTVD 289 | 290 FEAFGWDWII 299 | Chicken |
| 270 LDCDEHSTES 279 | 280 RCCRYPLTVD 289 | 290 FEAFGWDWII 299 | Turkey |
| 269 LDCDENSSES 278 | 279 RCCRYPLTVD 288 | 289 FEDFGWDWII 298 | Zebrafish |
| | | | |
| 301 APKRYKANYC 310 | 311 SGECE FV FLQ 320 | 321 KYPHTHLVHQ 330 | Mouse |
| 301 APKRYKANYC 310 | 311 SGECE FV FLQ 320 | 321 KYPHTHLVHQ 330 | Rat |
| 300 APKRYKANYC 309 | 310 SGECE FV FLQ 319 | 320 KYPHTHLVHQ 329 | Human |
| 300 APKRYKANYC 309 | 310 SGECE FV FLQ 319 | 320 KYPHTHLVHQ 329 | Baboon |
| 300 APKRYKANYC 309 | 310 SGECE FV FLQ 319 | 320 KYPHTHLVHQ 329 | Bovine |
| 300 APKRYKANYC 309 | 310 SGECE FV FLQ 319 | 320 KYPHTHLVHQ 329 | Porcine |
| 300 APKRYKANYC 309 | 310 SGECE FL FLQ 319 | 320 KYPHTHLVHQ 329 | Ovine |
| 300 APKRYKANYC 309 | 310 SGECE FV FLQ 319 | 320 KYPHTHLVHQ 329 | Chicken |
| 300 APKRYKANYC 309 | 310 SGECE FV FLQ 319 | 320 KYPHTHLVHQ 329 | Turkey |
| 299 APKRYKANYC 308 | 309 SGECDYMYLQ 318 | 319 KYPHTHLVNK 328 | Zebrafish |
| | | | |
| 331 ANPRGSAGPC 340 | 341 CTPTKMSPIN 350 | 351 MLYFNGKEQI 360 | Mouse |
| 331 ANPRGSAGPC 340 | 341 CTPTKMSPIN 350 | 351 MLYFNGKEQI 360 | Rat |
| 330 ANPRGSAGPC 339 | 340 CTPTKMSPIN 349 | 350 MLYFNGKEQI 359 | Human |
| 330 ANPRGSAGPC 339 | 340 CTPTKMSPIN 349 | 350 MLYFNGKEQI 359 | Baboon |
| 330 ANPRGSAGPC 339 | 340 CTPTKMSPIN 349 | 350 MLYFNGEGQI 359 | Bovine |
| 330 ANPRGSAGPC 339 | 340 CTPTKMSPIN 349 | 350 MLYFNGKEQI 359 | Porcine |
| 330 ANPKGSAGPC 339 | 340 CTPTKMSPIN 349 | 350 MLYFNGKEQI 359 | Ovine |
| 330 ANPRGSAGPC 339 | 340 CTPTKMSPIN 349 | 350 MLYFNGKEQI 359 | Chicken |
| 330 ANPRGSAGPC 339 | 340 CTPTKMSPIN 349 | 350 MLYFNGKEQI 359 | Turkey |
| 329 ASPRGTAGPC 338 | 339 CTPTKMSPIN 248 | 349 MLYFNGKEQI 359 | Zebrafish |

FIG. 1C

361 IYGKIPAMVV 370   371 DRCGCS 376 Mouse
361 IYGKIPAMVV 370   371 DRCGCS 376 Rat
360 IYGKIPAMVV 369   370 DRCGCS 375 Human
360 IYGKIPAMVV 369   370 DRCGCS 375 Baboon
360 IYGKIPAMVV 369   370 DRCGCS 375 Bovine
360 IYGKIPAMVV 369   370 DRCGCS 375 Porcine
360 IYGKIPGMVV 369   370 DRCGCS 375 Ovine
360 IYGKIPAMVV 369   370 DRCGCS 375 Chicken
360 IYGKIPAMVV 369   370 DRCGCS 375 Turkey
359 IYGKIP SMVV 368  369 DRCGCS 374 Zebrafish

FIG. 1D

```
          10            20            30            40
           |             |             |             |
GGA TCC CGT TCT CGT CGC GAC TTT GGT CTG GAC TGC GAC GAA CAT
Gly Ser Arg Ser Arg Arg Asp Phe Gly Leu Asp Cys Asp Glu His 50            60
     |             |
TCT ACC GAA AGA TCT
Ser Thr Glu Arg Ser                    FIG. 2
```

```
          10            20            30            40
           |             |             |             |
GGA TCC TCT CGT TGC TGT CGC TAT CCG CTG ACC GTT GAC TTC GAA
Gly Ser Ser Arg Cys Cys Arg Tyr Pro Leu Thr Val Asp Phe Glu

50
     |
AGA TCT
Arg Ser                                FIG. 3
```

```
          10            20            30            40
           |             |             |             |
GGA TCC TTC GAA GCT TTT GGT TGG GAC TGG ATC ATT GCA CCG AAA
Gly Ser Phe Glu Ala Phe Gly Trp Asp Trp Ile Ile Ala Pro Lys

50
     |
CGT TAT AGA TCT
Arg Tyr Arg Ser                        FIG. 4
```

```
         10          20          30          40
          |           |           |           |
GGA TCC AAA CGT TAT AAA GCT AAC TAT TGC TCT GGT GAA TGC GAA
Gly Ser Lys Arg Tyr Lys Ala Asn Tyr Cys Ser Gly Glu Cys Glu

50
  |
TTC AGA TCT
Phe Arg Ser
```

FIG. 5

```
         10          20          30          40
          |           |           |           |
GGA TCC GAA TTC GTT TTC CTG CAG AAA TAT CCG CAT ACC CAT CTG
Gly Ser Glu Phe Val Phe Leu Gln Lys Tyr Pro His Thr His Leu 50          60          70
  |           |           |
GTT CAT CAG GCT AAC CCG CGT AGA TCT
Val His Gln Ala Asn Pro Arg Arg Ser
```

FIG. 6

```
         10          20          30          40
          |           |           |           |
GGA TCC GCT GGT CCG TGC TGT TAT CCG ACC AAA ATG TCT CCG ATC
Gly Ser Ala Gly Pro Cys Cys Tyr Pro Thr Lys MET Ser Pro Ile 50          60          70          80
  |           |           |           |
AAC ATG CTG TAT TTC AAC GGT GAA TGC CAG AGA TCT
Asn MET Leu Tyr Phe Asn Gly Glu Cys Gln Arg Ser
```

FIG. 7

```
            10              20              30              40
             |               |               |               |
GGA TCC GAA TGC CAG ATC ATT TAT TGC AAA ATC CCG GCT ATG GTT
Gly Ser Glu Cys Gln Ile Ile Tyr Cys Lys Ile Pro Ala MET Val 50              60              70
             |               |               |
GTA GAC CGT TGC GGT TGT TCT AGA TCT
Val Asp Arg Cys Gly Cys Ser Arg Ser
```

FIG. 8

```
            10              20              30              40
             |               |               |               |
GGA TCC GAA CAG AAA GAA AAC GTT GAA AAA GAA GGT CTG TGC AAC
Gly Ser Glu Gln Lys Glu Asn Val Glu Lys Glu Gly Leu Cys Asn 50              60
             |               |
GCT TGC CTG TGG AGA TCT
Ala Cys Leu Trp Arg Ser
```

FIG. 9

```
            10              20              30              40
             |               |               |               |
GGA TCC CAT GAC CTG GCT GTT ACC TTC CCG GAA CCG GGT GAA GAC
Gly Ser His Asp Leu Ala Val Thr Phe Pro Glu Pro Gly Glu Asp 50              60
             |               |
GGT CTG ACC AGA TCT
Gly Leu Thr Arg Ser
```

FIG. 10

```
              10             20             30             40
GGA TCC ACC CCG TTC CTG GAA GTT AAA GTT ACC GAC ACT CCG AAA
Gly Ser Thr Pro Phe Leu Glu Val Lys Val Thr Asp Thr Pro Lys 50             60
CGT TCT CGT AGA TCT
Arg Ser Arg Arg Ser
```

FIG. 11

Entire Myostatin Protein
1 ─────────────────────────────────────────── 376

264  Myostatin Active Region 376
15____        17____  1____            13____
              19____  3____      11____
                       5____  9____
                         7____

FIG. 12

```
         10              20              30              40
          |               |               |               |
GGA TCC CGT TCT CGT CGC GAC TTT GGT CTG GAC TGC GAC GAA CAT
Gly Ser Arg Ser Arg Arg Asp Phe Gly Leu Asp Cys Asp Glu His 50              60              70              80              90
          |               |               |               |               |
TCT ACC GAA AGA TCC TCT CGT TGC TGT CGC TAT CCG CTG ACC GTT
Ser Thr Glu Arg Ser Ser Arg Cys Cys Arg Tyr Pro Leu Thr Val 100             110             120             130
          |               |               |               |
GAC TTC GAA GCT TTT GGT TGG GAC TGG ATC ATT GCA CCG AAA CGT
Asp Phe Glu Ala Phe Gly Trp Asp Trp Ile Ile Ala Pro Lys Arg 140             150             160             170             180
          |               |               |               |               |
TAT AGA TCC AAA CGT TAT AAA GCT AAC TAT TGC TCT GGT GAA TGC
Tyr Arg Ser Lys Arg Tyr Lys Ala Asn Tyr Cys Ser Gly Glu Cys 190             200             210             220
          |               |               |               |
GAA TTC GTT TTC CTG CAG AAA TAT CCG CAT ACC CAT CTG GTT CAT
Glu Phe Val Phe Leu Gln Lys Tyr Pro His Thr His Leu Val His 230             240             250             260             270
          |               |               |               |               |
CAG GCT AAC CCG CGT AGA TCC GCT GGT CCG TGC TGT TAT CCG ACC
Gln Ala Asn Pro Arg Arg Ser Ala Gly Pro Cys Cys Tyr Pro Thr 280             290             300             310
          |               |               |               |
AAA ATG TCT CCG ATC AAC ATG CTG TAT TTC AAC GGT GAA TGC CAG
Lys MET Ser Pro Ile Asn MET Leu Tyr Phe Asn Gly Glu Cys Gln 320             330             340             350             360
          |               |               |               |               |
ATC ATT TAT TGC AAA ATC CCG GCT ATG GTT GTA GAC CGT TGC GGT
Ile Ile Tyr Cys Lys Ile Pro Ala MET Val Val Asp Arg Cys Gly

370
          |
TGT TCT AGA TCT
Cys Ser Arg Ser
```

FIG. 13

```
   1870         1880         1890         1900         1910
    |            |            |            |            |
   ATG GCT ACT GTT ATA GAT CTA AGC TTC CCA AAA ACT GGG GCA AAA
   MET Ala Thr Val Ile Asp Leu Ser Phe Pro Lys Thr Gly Ala Lys 1920         1930         1940         1950
          |            |            |            |
   AAA ATT ATC CTC TAT ATT CCC CAA AAT TAC CAA TAT GAT ACT GAA
   Lys Ile Ile Leu Tyr Ile Pro Gln Asn Tyr Gln Tyr Asp Thr Glu 1960         1970         1980         1990         2000
    |            |            |            |            |
   CAA GGT AAT GGT TTA CAG GAT TTA GTC AAA GCG GCC GAA GAG TTG
   Gln Gly Asn Gly Leu Gln Asp Leu Val Lys Ala Ala Glu Glu Leu 2010         2020         2030         2040
          |            |            |            |
   GGG ATT GAG GTA CAA AGA GAA GAA CGC AAT AAT ATT GCA ACA GCT
   Gly Ile Glu Val Gln Arg Glu Glu Arg Asn Asn Ile Ala Thr Ala 2050         2060         2070         2080         2090
    |            |            |            |            |
   CAA ACC AGT TTA GGC ACG ATT CAA ACC GCT ATT GGC TTA ACT GAG
   Gln Thr Ser Leu Gly Thr Ile Gln Thr Ala Ile Gly Leu Thr Glu 2100         2110         2120         2130
          |            |            |            |
   CGT GGC ATT GTG TTA TCC GCT CCA CAA ATT GAT AAA TTG CTA CAG
   Arg Gly Ile Val Leu Ser Ala Pro Gln Ile Asp Lys Leu Leu Gln 2140         2150         2160         2170         2180
    |            |            |            |            |
   AAA ACT AAA GCA GGC CAA GCA TTA GGT TCT GCC GAA AGC ATT GTA
   Lys Thr Lys Ala Gly Gln Ala Leu Gly Ser Ala Glu Ser Ile Val 2190         2200         2210         2220
          |            |            |            |
   CAA AAT GCA AAT AAA GCC AAA ACT GTA TTA TCT GGC ATT CAA TCT
   Gln Asn Ala Asn Lys Ala Lys Thr Val Leu Ser Gly Ile Gln Ser 2230         2240         2250         2260         2270
    |            |            |            |            |
   ATT TTA GGC TCA GTA TTG GCT GGA ATG GAT TTA GAT GAG GCC TTA
   Ile Leu Gly Ser Val Leu Ala Gly MET Asp Leu Asp Glu Ala Leu
```

FIG. 15A

```
      2280            2290            2300            2310
       |               |               |               |
CAG AAT AAC AGC AAC CAA CAT GCT CTT GCT AAA GCT GGC TTG GAG
Gln Asn Asn Ser Asn Gln His Ala Leu Ala Lys Ala Gly Leu Glu 2320            2330            2340            2350            2360
  |               |               |               |               |
CTA ACA AAT TCA TTA ATT GAA AAT ATT GCT AAT TCA GTA AAA ACA
Leu Thr Asn Ser Leu Ile Glu Asn Ile Ala Asn Ser Val Lys Thr 2370            2380            2390            2400
           |               |               |               |
CTT GAC GAA TTT GGT GAG CAA ATT AGT CAA TTT GGT TCA AAA CTA
Leu Asp Glu Phe Gly Glu Gln Ile Ser Gln Phe Gly Ser Lys Leu 2410            2420            2430            2440            2450
  |               |               |               |               |
CAA AAT ATC AAA GGC TTA GGG ACT TTA GGA GAC AAA CTC AAA AAT
Gln Asn Ile Lys Gly Leu Gly Thr Leu Gly Asp Lys Leu Lys Asn 2460            2470            2480            2490
           |               |               |               |
ATC GGT GGA CTT GAT AAA GCT GGC CTT GGT TTA GAT GTT ATC TCA
Ile Gly Gly Leu Asp Lys Ala Gly Leu Gly Leu Asp Val Ile Ser 2500            2510            2520            2530            2540
  |               |               |               |               |
GGG CTA TTA TCG GGC GCA ACC GCT GCA CTT GTA CTT GCA GAT AAA
Gly Leu Leu Ser Gly Ala Thr Ala Ala Leu Val Leu Ala Asp Lys 2550            2560            2570            2580
           |               |               |               |
AAT GCT TCA ACA GCT AAA AAA GTG GGT GCG GGT TTT GAA TTG GCA
Asn Ala Ser Thr Ala Lys Lys Val Gly Ala Gly Phe Glu Leu Ala 2590            2600            2610            2620            2630
  |               |               |               |               |
AAC CAA GTT GTT GGT AAT ATT ACC AAA GCC GTT TCT TCT TAC ATT
Asn Gln Val Val Gly Asn Ile Thr Lys Ala Val Ser Ser Tyr Ile 2640            2650            2660            2670
           |               |               |               |
TTA GCC CAA CGT GTT GCA GCA GGT TTA TCT TCA ACT GGG CCT GTG
Leu Ala Gln Arg Val Ala Ala Gly Leu Ser Ser Thr Gly Pro Val
```

FIG. 15B

```
       2680           2690           2700           2710           2720
        |              |              |              |              |
      GCT GCT TTA ATT GCT TCT ACT GTT TCT CTT GCG ATT AGC CCA TTA
      Ala Ala Leu Ile Ala Ser Thr Val Ser Leu Ala Ile Ser Pro Leu 2730           2740           2750           2760
               |              |              |              |
      GCA TTT GCC GGT ATT GCC GAT AAA TTT AAT CAT GCA AAA AGT TTA
      Ala Phe Ala Gly Ile Ala Asp Lys Phe Asn His Ala Lys Ser Leu 2770           2780           2790           2800           2810
        |              |              |              |              |
      GAG AGT TAT GCC GAA CGC TTT AAA AAA TTA GGC TAT GAC GGA GAT
      Glu Ser Tyr Ala Glu Arg Phe Lys Lys Leu Gly Tyr Asp Gly Asp 2820           2830           2840           2850
               |              |              |              |
      AAT TTA TTA GCA GAA TAT CAG CGG GGA ACA GGG ACT ATT GAT GCA
      Asn Leu Leu Ala Glu Tyr Gln Arg Gly Thr Gly Thr Ile Asp Ala 2860           2870           2880           2890           2900
        |              |              |              |              |
      TCG GTT ACT GCA ATT AAT ACC GCA TTG GCC GCT ATT GCT GGT GGT
      Ser Val Thr Ala Ile Asn Thr Ala Leu Ala Ala Ile Ala Gly Gly 2910           2920           2930           2940
               |              |              |              |
      GTG TCT GCT GCT GCA GCC GAT TTA ACA TTT GAA AAA GTT AAA CAT
      Val Ser Ala Ala Ala Ala Asp Leu Thr Phe Glu Lys Val Lys His 2950           2960           2970           2980           2990
        |              |              |              |              |
      AAT CTT GTC ATC ACG AAT AGC AAA AAA GAG AAA GTG ACC ATT CAA
      Asn Leu Val Ile Thr Asn Ser Lys Lys Glu Lys Val Thr Ile Gln 3000           3010           3020           3030
               |              |              |              |
      AAC TGG TTC CGA GAG GCT GAT TTT GCT AAA GAA GTG CCT AAT TAT
      Asn Trp Phe Arg Glu Ala Asp Phe Ala Lys Glu Val Pro Asn Tyr 3040           3050           3060           3070           3080
        |              |              |              |              |
      AAA GCA ACT AAA GAT GAG AAA ATC GAA GAA ATC ATC GGT CAA AAT
      Lys Ala Thr Lys Asp Glu Lys Ile Glu Glu Ile Ile Gly Gln Asn
```

FIG. 15C

```
      3090          3100          3110          3120
       |             |             |             |
GGC GAG CGG ATC ACC TCA AAG CAA GTT GAT GAT CTT ATC GCA AAA
Gly Glu Arg Ile Thr Ser Lys Gln Val Asp Asp Leu Ile Ala Lys 3130          3140          3150          3160          3170
   |             |             |             |             |
GGT AAC GGC AAA ATT ACC CAA GAT GAG CTA TCA AAA GTT GTT GAT
Gly Asn Gly Lys Ile Thr Gln Asp Glu Leu Ser Lys Val Val Asp 3180          3190          3200          3210
       |             |             |             |
AAC TAT GAA TTG CTC AAA CAT AGC AAA AAT GTG ACA AAC AGC TTA
Asn Tyr Glu Leu Leu Lys His Ser Lys Asn Val Thr Asn Ser Leu 3220          3230          3240          3250          3260
   |             |             |             |             |
GAT AAG TTA ATC TCA TCT GTA AGT GCA TTT ACC TCG TCT AAT GAT
Asp Lys Leu Ile Ser Ser Val Ser Ala Phe Thr Ser Ser Asn Asp 3270          3280          3290          3300
       |             |             |             |
TCG AGA AAT GTA TTA GTG GCT CCA ACT TCA ATG TTG GAT CAA AGT
Ser Arg Asn Val Leu Val Ala Pro Thr Ser MET Leu Asp Gln Ser 3310          3320          3330          3340
   |             |             |             |
TTA TCT TCT CTT CAA TTT GCT AGG GGA TCC TAG
Leu Ser Ser Leu Gln Phe Ala Arg Gly Ser ---
```

FIG. 15D

```
   1 ATGCAAAAAC TGCAAATCTC TGTTTATATT TACCTATTTA CGCTGATTGT
  51 TGCTGGCCCA GTGGATCTGA ATGAGAACAG CGAGCAGAAG GAAAATGTGG
 101 AAAAGAGGG ACTGTGTAAT GCATGTTTGT GGAGGGAAAA CACTACATCC
 151 TCAAGACTAG AAGCCATAAA AATCCAAATC CTCAGTAAAC TTCGCCTGGA
 201 AACAGCTCCT AACATCAGCA AAGATGCTAT CAGACAACTT TTGCCCAAGG
 251 CTCCTCCACT CCTGGAACTG ATTGATCAGT TCGATGTCCA GAGAGATGCC
 301 AGCAGTGACG GCTCCTTGGA AGACGATGAC TACCACGCCA GGACGGAAAC
 351 GGTCATTACC ATGCCCACGG AGTCTGATCT TCTAACGCAA GTGGAAGGAA
 401 AACCCAAATG TTGCTTCTTT AAATTTAGCT CTAAGATACA ATACAATAAA
 451 CTAGTAAAGG CCCAACTGTG GATATATCTG AGGCCTGTCA AGACTCCTGC
 501 GACAGTGTTT GTGCAAATCC TGAGACTCAT CAAACCCATG AAAGACGGTA
 551 CAAGGTATAC TGGAATCCGA TCTCTGAAAC TTGACATGAA CCCAGGCACT
 601 GGTATTTGGC AGAGCATTGA TGTGAAGACA GTGTTGCAGA ACTGGCTCAA
 651 ACAACCTGAA TCCAACTTAG GCATTGAAAT CAAAGCTTTA GATGAGAATG
 701 GCCATGATCT TGCTGTAACC TTCCCAGAAC CAGGAGAAGA TGGACTGACT
 751 CCTTTTTTAG AAGTCAAGGT AACAGACACA CCAAAAAGAT CTAGGAGAGA
 801 TTTTGGGCTT GATTGTGATG AACACTCCAC AGAATCTCGA TGCTGTCGCT
 851 ACCCCCTCAC GGTGGATTTT GAAGCTTTTG GATGGGATTG GATTATTGCA
 901 CCTAAAAGAT ATAAGGCCAA TTACTGCTCT GGAGAATGTG AATTTGTATT
 951 TTTGCAAAAG TATCCTCATA CCCATCTTGT GCACCAAGCA AACCCCAGAG
1001 GTTCAGCCGG CCCCTGCTGT ACTCCTACAA AGATGTCTCC AATTAATATG
1051 CTATATTTTA ATGGCGAAGG ACAAATAATA TACGGGAAGA TTCCAGCCAT
1101 GGTAGTAGAT CGCTGTGGGT GCTCATGA
```

FIG. 16A

```
   1 MQKLQISVYI YLFTLIVAGP VDLNENSEQK ENVEKEGLCN ACLWRENTTS
  51 SRLEAIKIQI LSKLRLETAP NISKDAIRQL LPKAPPLLEL IDQFDVQRDA
 101 SSDGSLEDDD YHARTETVIT MPTESDLLTQ VEGKPKCCFF KFSSKIQYNK
 151 LVKAQLWIYL RPVKTPATVF VQILRLIKPM KDGTRYTGIR SLKLDMNPGT
 201 GIWQSIDVKT VLQNWLKQPE SNLGIEIKAL DENGHDLAVT FPEPGEDGLT
 251 PFLEVKVTDT PKRSRRDFGL DCDEHSTESR CCRYPLTVDF EAFGWDWIIA
 301 PKRYKANYCS GECEFVFLQK YPHTHLVHQA NPRGSAGPCC TPTKMSPINM
 351 LYFNGEGQII YGKIPAMVVD RCGCS
```

FIG. 16B

MYOSTATIN MULTIMERS

CROSS-REFERENCE TO RELATED APPLICATION

This application is related to provisional patent application serial No. 60/075,213, filed Feb. 19, 1998, from which priority is claimed under 35 USC §119(e)(1) and which is incorporated herein by reference in its entirety.

TECHNICAL FIELD

The present invention relates generally to compositions and methods for increasing muscle synthesis and treating disease in vertebrate subjects. More particularly, the invention is directed to immunological compositions and methods for reducing myostatin activity in vertebrate subjects.

BACKGROUND OF THE INVENTION

Livestock producers have traditionally used breeding programs to select animals that yield maximum amounts of protein with acceptable performance as measured by feed efficiency, reproductive function and general health. Cattle which exhibit increased muscle mass due to both hypertrophy and hyperplasia of muscle cells have been observed in a number of breeds. The incidence of this condition, which is referred to as double-muscling, is most pronounced in Belgian Blue cattle. Muscle mass is increased by approximately 20% with a decrease in bone and fat mass in these animals (Shahin and Berg, Can. J. Anim. Sci. (1985) 65:279–293). Belgian Blue cattle also utilize feed efficiently and give rise to a higher percentage of desirable cuts of meat (Casas et al., J. Anim. Sci. (1997) 75(Supp 1):149). Double-muscling in Belgian Blue cattle is inherited and is believed to be recessive since heterozygotes may be normal or have only a modest increase in muscle mass.

Despite the advantages of this condition, double-muscled cattle often have undesirable traits. For example, because calves are generally 10–38% heavier than normal, dystocias are prevalent, requiring cesarean deliveries. Animals also exhibit abnormal reproduction due to poorly developed reproductive tracts and have other anatomical abnormalities such as macroglossia. Other breeds of cattle, such as the Piemontese from northern Italy, have varying degrees of double-muscling and also display many of these undesirable traits.

The double-muscling characteristic identified in some cattle breeds has now been traced to mutations in the myostatin gene (Grobet et al., Nature Genetics (1997) 17:71–74; Kambadur et al., Genome Research (1997) 7:910–915; McPherron and Lee, Proc. Natl. Acad. Sci. USA (1997) 94:12457–12461). This mutation appears to result mainly in an increase in the number of muscle cells (hyperplasia) rather than an increase in the size of individual muscle fibers (hypertrophy). A condition referred to as muscular hypertrophy has also been identified in the Pietrain breed of pig. This condition is not related to the myostatin gene and has been identified as a mutation in a gene responsible for calcium transport.

McPherron et al., Nature (1997) 387:83–90, have identified a member of the transforming growth factor-β (TGF-β) superfamily of proteins in mice, referred to as growth/differentiating factor-8 (GDF-8). GDF-8 acts as a negative regulator for skeletal muscle growth and is expressed in developing and adult skeletal muscles. Gene knockout experiments in mice have resulted in homozygous mutants which are 30% larger than wild-type mice. This increase in size is due primarily to an increase in muscle mass with individual muscles from the mutants weighing 2–3 times more than those from wild-type mice (McPherron et al., Nature (1997) 387:83–90). McPherron and Lee, Proc. Natl. Acad. Sci. USA (1997) 94:12457–12461 and Grobet et al., Nature Genetics (1997) 17:71–74 evaluated similar genomic sequences in a number of species, including cattle, and reported that double-muscled cattle had defects in the gene coding for a protein highly homologous to GDF-8. This protein is now called myostatin.

Thus, it appears that myostatin is produced by muscle cells and regulates the proliferation and differentiation of myoblasts. In Belgian Blue and Piemontese cattle, natural defects in the gene are believed to result either in production of an abnormal protein or a reduced amount of myostatin, either of which has the effect of increasing muscle growth.

The myostatin gene from a number of vertebrate species, including mouse, rat, human, baboon, cattle, pig, sheep, chicken, turkey, and zebrafish has been identified and the proteins sequenced (McPherron and Lee, Proc. Natl. Acad. Sci. USA (1997) 94:12457–12461). The myostatin protein sequence is highly conserved across all of these species. Similarly, the nucleotide sequence for myostatin from mouse, rat, human, baboon, cattle, pig, sheep, chicken and turkey has been determined. See, e.g., U.S. Pat. No. 5,827,733 for the nucleotide sequences of murine and human myostatin; International Publication No. WO 99/02667 for the nucleotide sequence of bovine myostatin; International Publication No. WO 98/33887, for the nucleotide sequences of rat, human, baboon, bovine, porcine, ovine, chicken and turkey myostatin.

The nucleotide sequence of the myostatin gene predicts a protein of about 376 amino acids with a molecular weight of approximately 43 kDa. This protein contains a secretion leader sequence and a proteolytic processing site which releases a 13 kDa peptide, containing 9 cysteine residues. Cloned myostatin expressed in Chinese hamster ovary cells yields two proteins. The first has an apparent molecular weight of about 52 kDa and the second about 15 kDa. Under nonreducing conditions, these proteins appear to be dimers with molecular weights of about 101 kDa and 25 kDa (McPherron et al., Nature (1997) 387:83–90).

Researchers have proposed delivery of mutated myostatin genes to animal subjects for the production of transgenic species having increased muscle tissue. See, e.g., International Publication No. WO 98/33887. However, such approaches pose several drawbacks. For example, because the myostatin gene becomes active during the embryonic stage, reduced myostatin production causes excessive muscle development in utero. Thus, transgenic animals which include mutated genes would likely require cesarean delivery, a serious burden to large animal producers. Additionally, public opposition to genetically engineered animals for human consumption exists and other methods of producing such animals would be desirable.

DISCLOSURE OF THE INVENTION

The present invention is directed to immunological compositions and methods for modulating endogenous myostatin activity in a vertebrate subject. The invention is also useful for treating a number of conditions in vertebrates, including humans and other animals, such as a variety of disorders that cause degeneration or wasting of muscle. Due to the ubiquitous nature of myostatin, the compositions and methods described herein find use in a wide variety of vertebrate subjects, as described further below.

Surprisingly, the invention achieves these results by immunological techniques. It is readily known in the art that immunization against endogenous molecules, such as myostatin, is problematic because the immune system does not recognize such "self" molecules. Thus, the present invention provides a solution to a problem which would normally be encountered when immunizing against an endogenous substance.

Accordingly, in one embodiment, the invention is directed to a myostatin peptide consisting of about 3 to about 100 amino acids. The peptide comprises at least one epitope of myostatin. In preferred embodiments, the myostatin peptide is derived from the region of myostatin spanning amino acids 45 through 376, inclusive, of FIGS. 1A–1D (SEQ ID NOS:27–36) or amino acids 235 through 376, inclusive, of FIGS. 1A–1D (SEQ ID NOS:27–36).

In other embodiments, the myostatin peptide has at least about 75% amino acid identity to a peptide comprising an amino acid sequence selected from the group consisting of amino acids 3–18, inclusive of SEQ ID NO:4; amino acids 3–15, inclusive of SEQ ID NO:6; amino acids 3–17, inclusive, of SEQ ID NO:8; amino acids 3–16, inclusive of SEQ ID NO:10; amino acids 3–22, inclusive of SEQ ID NO:12; amino acids 3–25, inclusive of SEQ ID NO:14; amino acids 3–22, inclusive of SEQ ID NO:16; amino acids 3–18, inclusive of SEQ ID NO:20; and amino acids 3–18, inclusive, of SEQ ID NO:22.

In still further embodiments, the invention is directed to a myostatin peptide consisting of about 3 to about 200 amino acids. The peptide comprises at least one epitope of myostatin and is derived from a region of myostatin selected from the group consisting of the region of myostatin spanning amino acids 1 through 350, inclusive, of FIGS. 1A–1D (SEQ ID NOS:27–36); the region of myostatin spanning amino acids 1 through 275, inclusive, of FIGS. 1A–1D (SEQ ID NOS:27–36); the region of myostatin spanning amino acids 25 through 300, inclusive, of FIGS. 1A–1D (SEQ ID NOS:27–36); the region of myostatin spanning amino acids 50 through 325, inclusive, of FIGS. 1A–1D (SEQ ID NOS:27–36); and the region of myostatin spanning amino acids 75 through 350, inclusive, of FIGS. 1A–1D (SEQ ID NOS:27–36).

In yet further embodiments, the myostatin peptide comprises the amino acid sequence Lys-Arg-Ser-Arg-Arg-Asp (SEQ ID NO:37), the amino acid sequence Lys-Glu-Asn-Val-Glu-Lys-Glu (SEQ ID NO:38) or the amino acid sequence Ser-Leu-Lys-Asp-Asp-Asp (SEQ ID NO:39).

In yet another embodiment, the invention is directed to a myostatin multimer comprising two or more selected myostatin immunogens, wherein each of the immunogens independently comprises at least 3 amino acids defining at least one epitope of myostatin. In particularly preferred embodiments, each of the selected myostatin immunogens comprises at least one epitope of myostatin and independently consists of about 3 to about 200 amino acids, or about 3 to about 100 amino acids, or about 3 to about 30 amino acids, or about 3 to about 15 amino acids.

In other embodiments, each of the selected myostatin immunogens in the multimer independently comprise a selected myostatin peptide as described above. In particularly preferred embodiments, the multimer comprises a molecule with repeating units according to the general formula (MP-X-MP)y, wherein MP is a myostatin peptide, X is selected from the group consisting of a peptide linkage, an amino acid spacer group, a leukotoxin polypeptide and $[MP]_n$, where n is greater than or equal to 1, and y is greater than or equal to 1.

In another embodiment, the invention is directed to a myostatin immunoconjugate comprising at least one myostatin peptide or multimer, as described above, linked to an immunological carrier.

In still further embodiments, the invention is directed to vaccine compositions comprising the myostatin peptide, the myostatin multimer and/or the myostatin immunoconjugate, and a pharmaceutically acceptable excipient.

In yet other embodiments, the invention is directed to polynucleotides encoding the myostatin peptides., the myostatin multimers and the myostatin immunoconjugates above, as well as recombinant vectors comprising the polynucleotides, host cells transformed with the recombinant vectors, and methods of recombinantly producing the myostatin peptides, myostatin multimers and myostatin immunoconjugates.

In other embodiments, the invention is directed to methods of eliciting an immune response against a myostatin immunogen in a vertebrate subject comprising administering the vaccine compositions or polynucleotides above to the vertebrate subject. In particularly preferred embodiments, the immune response elicited reduces endogenous myostatin activity in the vertebrate subject and results in at least one of the following biological effects:

(a) an increase in body weight;
(b) an increase in muscle mass;
(c) an increase in the number of muscle cells;
(d) an increase in the size of muscle cells;
(e) a reduction in body fat content;
(f) an increase in muscle strength;
(g) an increase in mammary gland tissue;
(h) an increase in lactation;
(i) an increase in appetite or feed uptake; or
(j) an increase in the life span of the vertebrate subject.

In other embodiments, the invention is directed to methods of treating a disorder which comprises degeneration or wasting of muscle in a vertebrate subject, the method comprising administering the vaccine compositions or polynucleotides above to the subject. The invention is also directed to methods of modulating GDF11 activity in a vertebrate subject comprising administering the vaccine compositions above.

These and other embodiments of the present invention will readily occur to those of ordinary skill in the art in view of the disclosure herein.

BRIEF DESCRIPTION OF THE FIGURE

FIGS. 1A–1D show a comparison of myostatin derived from various species as follows: Mouse (SEQ ID NO:27); Rat (SEQ ID NO:28); Human (SEQ ID NO:29); Baboon (SEQ ID NO:30); Bovine (SEQ ID NO:31); Porcine (SEQ ID NO:32); Ovine (SEQ ID NO:33); Chicken (SEQ ID NO:34); Turkey (SEQ ID NO:35); and Zebrafish (SEQ ID NO:36). Amino acids are numbered to the right and left of the sequences.

FIG. 2 shows the nucleotide sequence (SEQ ID NO:3) and corresponding amino acid sequence (SEQ ID NO:4) of the MYOS 1 peptide. MYOS 1 includes the proteolytic cleavage site, Arg-Ser-Arg-Arg, and the N-terminus of the active protein.

FIG. 3 depicts the nucleotide sequence (SEQ ID NO:5) and corresponding amino acid sequence (SEQ ID NO:6) of the MYOS 3 peptide.

FIG. 4 depicts the nucleotide sequence (SEQ ID NO:7) and corresponding amino acid sequence (SEQ ID NO:8) of the MYOS 5 peptide.

FIG. 5 shows the nucleotide sequence (SEQ ID NO:9) and corresponding amino acid sequence (SEQ ID NO:10) of the MYOS 7 peptide.

FIG. 6 shows the nucleotide sequence (SEQ ID NO:11) and corresponding amino acid sequence (SEQ ID NO:12) of the MYOS 9 peptide.

FIG. 7 shows the nucleotide sequence (SEQ ID NO:13) and corresponding amino acid sequence (SEQ ID NO:14) of the MYOS 11 peptide.

FIG. 8 shows the nucleotide sequence (SEQ ID NO:15) and corresponding amino acid sequence (SEQ ID NO:16) of the MYOS 13 peptide.

FIG. 9 shows the nucleotide sequence (SEQ ID NO:17) and corresponding amino acid sequence (SEQ ID NO:18) of the MYOS 15 peptide.

FIG. 10 shows the nucleotide sequence (SEQ ID NO:19) and corresponding amino acid sequence (SEQ ID NO:20) of the MYOS 17 peptide.

FIG. 11 shows the nucleotide sequence (SEQ ID NO:21) and corresponding amino acid sequence (SEQ ID NO:22) of the MYOS 19 peptide. MYOS 19 includes the proteolytic cleavage site, Arg-Ser-Arg-Arg.

FIG. 12 shows the approximate position of MYOS peptides 1, 3, 5, 7, 9, 11, 13, 15, 17 and 19 within the myostatin sequence.

FIG. 13 shows the nucleotide sequence (SEQ ID NO:23) and corresponding amino acid sequence (SEQ ID NO:24) for a reconstructed myostatin active region containing three sets of two amino acid linkers (Arg-Ser) inserted in the sequence at nucleotide positions 55–60, 139–144 and 241–246 and at the C-terminus.

FIGS. 15A–15D show the nucleotide sequence (SEQ ID NO:25) and corresponding amino acid sequence (SEQ ID NO:26) of the leukotoxin carrier polypeptide present in plasmid pCB150. Myostatin oligo repeats are inserted into the BamH1 site present at nucleotide position 3334.

FIG. 16A shows the nucleotide sequence (SEQ ID NO:1) and FIG. 16B shows the predicted amino acid sequence (SEQ ID NO:2) of a representative myostatin for use with the present invention. The proteolytic cleavage site is found at positions 263–266 of FIG. 16B. The myostatin active region of the polypeptide spans amino acids 264–375.

DETAILED DESCRIPTION

Figure 14:
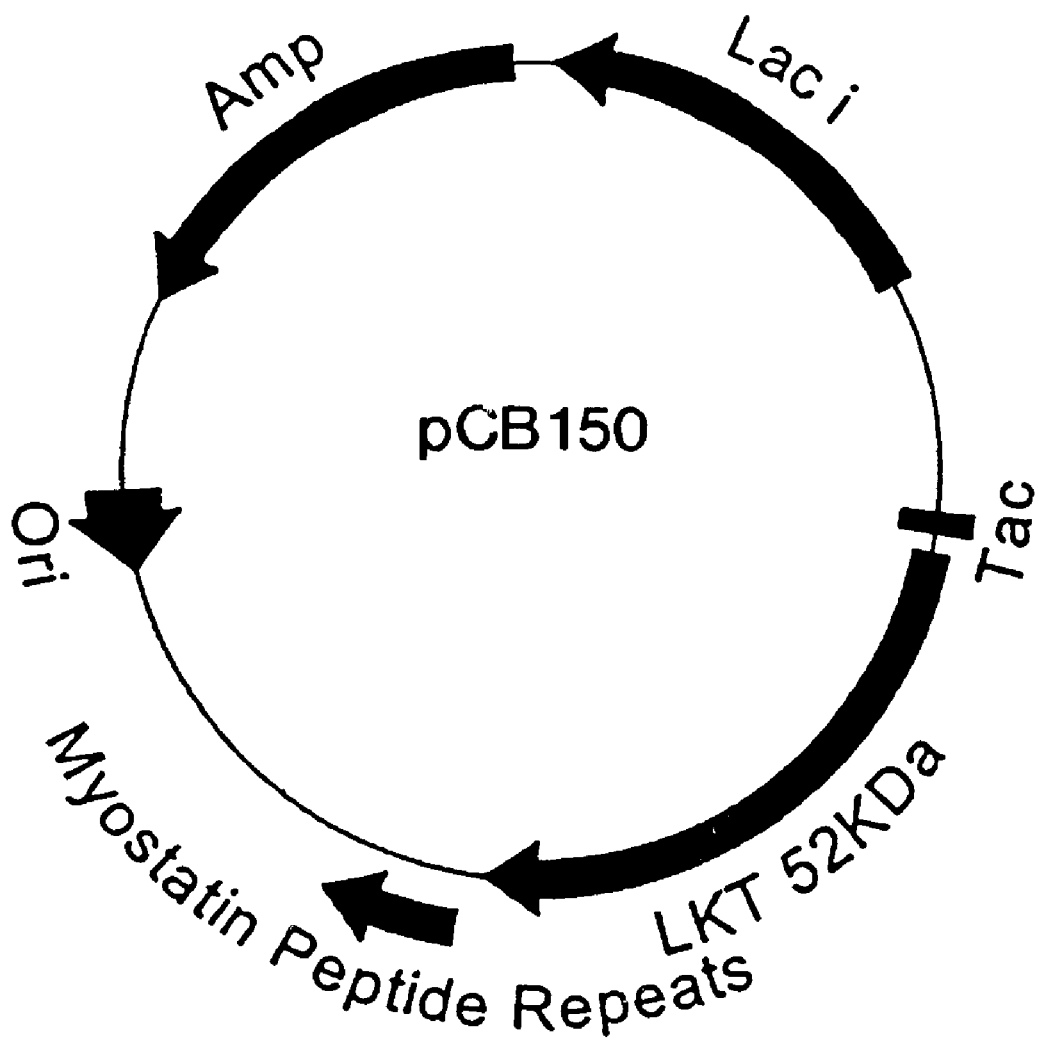
FIG. 14 is a diagram of plasmid pCB150, encoding a leukotoxin polypeptide carrier and used to create myostatin expression vectors as described in the examples.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual; DNA Cloning*, Vols. I and II (D. N. Glover ed.); *Oligonucleotide Synthesis* (M. J. Gait ed.); *Nucleic Acid Hybridization* (B. D. Hames & S. J. Higgins eds.); B. Perbal, *A Practical Guide to Molecular Cloning*; the series, *Methods In Enzymology* (S. Colowick and N. Kaplan eds., Academic Press, Inc.); and *Handbook of Experimental Immunology*, Vols. I–IV (D. M. Weir and C. C. Blackwell eds., Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

By "myostatin immunogen" is meant a polypeptide derived from a myostatin molecule which elicits an immunological response as defined below. The term includes molecules that elicit an immunological response without an associated immunological carrier, adjuvant or immunostimulant, as well as myostatin polypeptides capable of being rendered immunogenic, or more immunogenic, by way of association with a carrier molecule, adjuvant or immunostimulant, or by mutation of a native sequence, and/or by incorporation into a molecule containing multiple repeating units of at least one epitope of a myostatin molecule. The term may be used to refer to an individual macromolecule or to a homogeneous or heterogeneous population of antigenic macromolecules derived from myostatin.

For purposes of the present invention, a myostatin immunogen may be derived from any of the various known myostatin sequences, including without limitation, myostatin polypeptides derived from mouse, rat, human, baboon, cattle, pig, sheep, chicken, turkey, and zebrafish (see, McPherron and Lee, *Proc. Natl. Acad. Sci. USA* (1997) 94:12457–12461). The myostatin protein sequence is highly conserved across all of these species (see FIGS. 1A–1D).

Additionally, the term "myostatin immunogen" includes a myostatin polypeptide molecule differing from the reference sequence by having one or more amino acid substitutions, deletions and/or additions and which has at least about 50% amino acid identity to the reference molecule, more preferably about 75–85% identity and most preferably about 90–95% identity or more, to the relevant portion of the native peptide sequence in question. The amino acid sequence will have not more than about 10–20 amino acid substitutions, or not more than about 5–10 amino acid substitutions, or even only 1, 2, 3 or up to 5 substitutions. Particularly preferred substitutions will generally be conservative in nature, i.e., those substitutions that take place within a family of amino acids. In this regard, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the activity. Proteins having substantially the same amino acid sequence as the reference molecule, but possessing minor amino acid substitutions that do not substantially affect the immunogenicity of the protein, are therefore within the definition of a myostatin immunogen.

As used herein a "myostatin immunogen" also includes a molecule derived from a native myostatin sequence, as well as recombinantly produced or chemically synthesized myostatin polypeptides including the full-length myostatin reference sequence, as well as myostatin peptides which remain immunogenic, as described below.

A "myostatin immunogen" thus includes molecules having the native sequence, molecules with single or multiple amino acid additions, substitutions and/or deletions, as well as peptide fragments of the reference myostatin molecule, so long as the molecule retains the ability to elicit formation of antibodies that cross-react with the naturally occurring myostatin of the vertebrate species to which such an immunogen is delivered. Epitopes of myostatin are also captured by the definition.

A "myostatin peptide" is a myostatin immunogen, as described herein, which includes less than the full-length of the reference myostatin molecule in question and which includes at least one epitope as defined below. Thus, a vaccine composition comprising a myostatin peptide would include a portion of the full-length molecule but not the entire myostatin molecule in question.

By "myostatin multimer" is meant a molecule having more than one copy of a selected myostatin immunogen, myostatin peptide or epitope, or multiple tandem repeats of a selected myostatin immunogen, myostatin peptide or epitope. The myostatin multimer may correspond to a molecule with repeating units of the general formula (MP-X-MP)y wherein MP is a myostatin peptide, X is selected from the group consisting of a peptide linkage, an amino acid spacer group and $[MP]_n$, where n is greater than or equal to 1, y is greater than or equal to 1, and further wherein "MP" may comprise any MP peptide. Y may therefore define 1–40 or more repeating units, more preferably, 1–30 repeating units and most preferably, 1–20 repeating units. Further, the selected myostatin peptide sequences may all be the same, or may correspond to different derivatives, analogs, variants or epitopes of myostatin so long as they retain the ability to elicit an immune response. Additionally, if the myostatin peptides are linked either chemically or recombinantly to a carrier, myostatin peptides may be linked to either the 5'-end, the 3'-end, or may flank the carrier in question. Further, the myostatin multimer may be located at sites internal to the carrier. Myostatin multimers are discussed in further detail below.

"Homology" refers to the percent identity between two polynucleotide or two polypeptide moieties. Two DNA, or two polypeptide sequences are "substantially homologous" to each other when the sequences exhibit at least about 75%–85%, preferably at least about 90%, and most preferably at least about 95%–98% sequence identity over a defined length of the molecules. As used herein, substantially homologous also refers to sequences showing complete identity to the specified DNA or polypeptide sequence.

Percent "identity" between two amino acid or polynucleotide sequences can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M.O. in *Atlas of Protein Sequence and Structure* M.O. Dayhoff ed., 5 Suppl. 3:353–358, National biomedical Research Foundation, Washington, DC, which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, identity can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

An "immunological response" to an immunogen or vaccine is the development in the host of a cellular and/or antibody-mediated immune response to the immunogen or vaccine of interest. Usually, such a response includes but is not limited to one or more of the following effects; the production of antibodies, B cells, helper T cells, suppressor T cells, and/or cytotoxic T cells and/or γδ T cells, directed specifically to an immunogen or immunogens included in a composition or vaccine of interest. An immunological response can be detected using any of several assays well known in the art, such as standard immunoassays and neutralization assays, including Western blots, dot blots and immunoaffinity assays. The presence of a cell-mediated immunological responses may be determined using CTL cytotoxic cell assays, well known in the art, such as the assay described in Erickson et al. *J. Immunol.* (1993) 151:4189–4199; and Doe et al. *Eur. J. Immunol.* (1994) 24:2369–2376.

An "epitope" refers to any portion or region of a molecule with the ability or potential to elicit, and combine with, a myostatin-specific antibody. For the purpose of the present invention, a polypeptide epitope will usually include at least about 3 amino acids, preferably at least about 5 amino acids, and most preferably at least about 10–15 amino acids to 20–30 or more amino acids, of the reference molecule. There is no critical upper limit to the length of the fragment, which could comprise nearly the full-length of a protein sequence, or even a fusion protein comprising two or more epitopes of a protein in question.

Epitopes in polypeptide molecules can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Computer programs that formulate hydropathy scales from the amino acid sequence of the protein, utilizing the hydrophobic and hydrophilic properties of each of the 20 amino acids, as described in, e.g., Kyte et al., *J. Mol. Biol.* (1982) 157:105–132; and Hopp and Woods, *Proc. Natl. Acad. Sci. USA* (1981) 78:3824–3828, can also be used to determine antigenic portions of a given molecule. For example, the technique of Hopp and Woods assigns each amino acid a numerical hydrophilicity value and then repetitively averages these values along the peptide chain. The points of highest local average hydrophilicities are indicative of antigenic portions of the molecule.

By "immunological carrier" is meant any molecule which, when associated with a myostatin immunogen of interest, imparts immunogenicity to that molecule, or enhances the immunogenicity of the molecule. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactive virus particles; bacterial toxins such as toxoid from diphtheria, tetanus, cholera, leukotoxin molecules, and the like. Carriers are described in further detail below.

A myostatin immunogen is "linked" to a specified carrier molecule when the immunogen is chemically coupled to, or associated with the carrier, or when the immunogen is expressed from a chimeric DNA molecule which encodes the immunogen and the carrier of interest.

An "immunoconjugate" is a myostatin immunogen such as a myostatin peptide or multimer which is linked to a carrier molecule, as defined above.

The term "leukotoxin polypeptide" or "LKT polypeptide" intends a polypeptide which is derived from a protein belonging to the family of molecules characterized by the carboxy-terminus consensus amino acid sequence Gly-Gly-X-Gly-X-Asp (Highlander et al. (1989) DNA 8:15–28), wherein X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al. (1987) *Infect. Inmmun.* 55:3233–3236; Lo (1990) *Can. J. Vet. Res.* 54: S33–S35; Welch (1991) *Mol. Microbiol.* 5:521–528). This family of toxins is known as the "RTX" family of toxins (Lo (1990) *Can. J. Vet. Res.* 54: S33–S35). In addition, the term "leukotoxin polypeptide" refers to a leukotoxin polypeptide which is chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogues. Although native full-length leukotoxins display cytotoxic activity, the term "leukotoxin" also intends molecules which remain immunogenic yet lack the cytotoxic character of native leukotoxins. The nucleotide sequences and corresponding amino acid sequences for several leukotoxins are known. See, e.g., U.S. Pat. Nos. 4,957,739 and 5,055,400; Lo et al. (1985) *Infect. Immun.* 50:667–67; Lo et al. (1987) *Infect. Immun.* 55:1987–1996; Strathdee et al. (1987) Infect. Immun. 55:3233–3236; Highlander et al. (1989) *DNA* 8:15–28; and Welch (1991) *Mol. Microbiol.* 5:521–528. In preferred embodiments of the invention, leukotoxin chimeras are provided having a selected leukotoxin polypeptide sequence that imparts enhanced immunogenicity to one or more myostatin multimers fused thereto.

Particular examples of immunogenic leukotoxin polypeptides for use in the present invention are truncated leukotoxin molecules described in U.S. Pat. Nos. 5,476,657 and 5,837,268, incorporated herein by reference in their entireties. These truncated molecules include LKT 352, LKT 111 and LKT 114. LKT 352 is derived from the lktA gene present in plasmid pAA352 (ATCC Accession No. 68283). The nucleotide sequence and corresponding amino acid sequence of this gene are described in U.S. Pat. No. 5,476,657. The gene encodes a truncated leukotoxin, having 914 amino acids and an estimated molecular weight of around 99 kDa. LKT 111 is a leukotoxin polypeptide derived from the lktA gene present in plasmid pCB111 (ATCC Accession No. 69748). The nucleotide sequence of this gene and the corresponding amino acid sequence are disclosed in U.S. Pat. No. 5,837,268. The gene encodes a shortened version of leukotoxin which was developed from the recombinant leukotoxin gene present in plasmid pAA352 (ATCC Accession No. 68283) by removal of an internal DNA fragment of approximately 1300 bp in length. The LKT 111 polypeptide has an estimated molecular weight of 52 kDa (as compared to the 99 kDa LKT 352 polypeptide), but retains portions of the LKT 352 N-terminus containing T-cell epitopes which are necessary for sufficient T-cell immunogenicity, and portions of the LKT 352 C-terminus containing convenient restriction sites for use in producing fusion proteins for use in the present invention. LKT 114 is derived from the gene present in plasmid pAA114 (described in U.S. Pat. No. 5,837,268) and is shown in FIGS. 15A–15D herein. LKT 114 differs from LKT 111 by virtue of an additional amino acid deletion from the internal portion of the molecule.

"Adjuvants" refer to agents which act in a nonspecific manner to increase an immune response to a particular antigen, thus reducing the quantity of antigen necessary in any given vaccine, and/or the frequency of injection necessary in order to generate an adequate immune response to the antigen of interest. See, e.g., A. C. Allison *J. Reticuloendothel. Soc.* (1979) 26:619–630.

"Native" proteins, polypeptides or peptides are proteins, polypeptides or peptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

By "polynucleotide" is meant a sequence of nucleotides including, but is not limited to, RNA such as MRNA, cDNA, genomic DNA sequences and even synthetic DNA sequences. The term also captures sequences that include any of the known base analogs of DNA and RNA.

A "vector" is a replicon, such as a plasmid, phage, or cosmid, to which another DNA segment may be attached so as to bring about the replication of the attached segment.

A DNA "coding sequence" or a "sequence encoding" a particular protein, is a DNA sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

The term "derived from," as it is used herein, denotes an actual or theoretical source or origin of the subject molecule or immunogen. For example, an immunogen that is "derived from" a particular myostatin molecule will bear close sequence similarity with a relevant portion of the reference molecule. Thus, an immunogen that is "derived from" a particular myostatin molecule may include all of the wild-type myostatin sequence, or may be altered by insertion, deletion or substitution of amino acid residues, so long as the derived sequence provides for an immunogen that corresponds to the targeted myostatin molecule. Immunogens derived from a denoted molecule will contain at least one epitope specific to the denoted molecule.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age or gender. Thus, both male and female adult and newborn animals, as well as fetuses and eggs, are intended to be covered.

The compositions and methods of the present invention will serve to "reduce myostatin activity." This reduction in activity may be a reduction of circulating levels of myostatin normally found in a vertebrate subject, or a reduction of circulating levels of myostatin in subjects with disorders that result in elevated circulating levels of myostatin. A reduction in myostatin activity generally results from inactivation of circulating myostatin by antibodies generated against the myostatin peptide immunogen delivered to the subject in question. However, the reduction of activity is not limited to a particular mode of inactivation, but may be the result of decreased production or secretion of myostatin into the circulation. While not being bound by a particular theory, the myostatin peptide immunogens may elicit the production of antibodies which prevent myostatin from being cleaved to release the active portion of the protein, or prevent the protein from binding to its receptor. Alternatively, the antibodies may remove secreted myostatin from circulation or other body fluids before it reaches the active site.

The reduction in myostatin activity may manifest itself in a variety of ways. For example, reduction in myostatin activity may result in an increase in body weight, enhanced muscle mass, increased muscle strength, an alteration in the ratio of muscle to fat, an increase in fat-free muscle mass, an increase in the size and/or number of muscle cells, a reduction in body fat content, an increase in life span in a normal or diseased vertebrate, an increase in appetite or feed uptake, an enhanced quality of life, and in mammals, an increase in mammary gland tissue and lactation.

By "enhancing muscle mass" is meant that the animal administered a composition of the present invention displays an increase in muscle cell size (hypertrophy) or muscle cell numbers (hyperplasia). The increase can be in type 1 and/or type 2 muscle fibers. The term "muscle" as used herein is intended to capture analogous tissue types in fish. Methods for determining "enhanced muscle mass" are well known in the art. For example, muscle content can be measured before and after administration of a myostatin peptide of the invention using standard techniques, such as under water weighing (see, e.g., Bhasin et al. *New Eng. J. Med.* (1996) 335:1–7) and dual-energy x-ray absorptiometry (see, e.g., Bhasin et al. Mol. Endocrinol. (1998) 83:3155–3162). An increase in muscle size may be evidenced by weight gain of at least about 5–10%, preferably at least about 10–20% or more.

B. General Methods

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

Central to the instant invention is the development of immunological compositions and methods for modulating endogenous myostatin production in a vertebrate subject. Although myostatin is generally recognized as "self" and hence nonimmunogenic, the compositions described herein surprising provide a means for producing an immunological response in a subject immunized therewith.

Accordingly, the invention is directed to immunogenic myostatin peptides, myostatin multimers and myostatin immunoconjugates for use in generating an immune response in a vertebrate subject. Since the myostatin protein is secreted, active or passive immunization of young animals serves to increase muscle mass but avoids the problems associated with other abnormalities which arise from changes induced during the embryonic period. Thus, for example, vaccination schedules can be initiated shortly after birth to achieve both hypertrophy and/or hyperplasia. Alternatively, immunization can be done at a later stage of development, (e.g., to cattle in feedlots) to improve muscle protein yield. Additionally, immunization can be done prenatally or to animals in utero, to achieve the desired results.

The compositions and techniques described herein are equally applicable to egg-laying vertebrates, such as birds and fish. In this regard, McPherron and Lee, *Proc. Natl. Acad. Sci. USA* (1997) 94:12457–12461, have identified myostatin genes in birds and fish which are highly homologous to mammalian myostatin genes. Therefore, the gene is conserved among species and is believed to serve a similar function in all species. Thus, for example, egg-laying birds and fish are immunized to create high antibody titers in maternal plasma. Since antibodies are transferred to the yolk sac of the egg, these antibodies are able to reduce myostatin during the embryonic period and cause the desired increase in size and/or numbers of muscle cells. Alternatively, immunization may be done in ovo.

Furthermore, the methods and vaccines described herein will find use for the treatment of various disorders in humans and other animals. For example, modulation of myostatin production is useful for the treatment of individuals with disorders that either primarily or incidentally cause muscle wasting such as for the treatment of paraplegics and quadriplegics, where muscle atrophy is a serious concern. Elderly subjects may also benefit from the methods and vaccines described herein where lack of muscle strength is often a serious limitation to an active, healthy lifestyle. Additionally, the compositions of the present invention can be used to treat or prevent muscle wasting due to various cancers, anorexia, cachexia, AIDS, and like disorders.

The methods and vaccines of the present invention will find use for treating various dystrophies, such as pseudohypertrophic muscular dystrophies, facioscapulohumeral dystrophies, limb-girdle muscular dystrophies, distal muscular dystrophies, ocular myopathies, and myotonic dystrophies. These diseases include the disorders known as Becker's type muscular dystrophy, Dejerine-Landouzy muscular dystrophy, Duchenne's type muscular dystrophy, Landouzy muscular dystrophy, Emery-Dreifuss muscular dystrophy, Erb's muscular dystrophy, Fukuyama type muscular dystrophy, Gowers' muscular dystrophy, infantile neuroaxonal muscular dystrophy, Leyden-Mölus muscular dystrophy, oculopharyngeal muscular dystrophy, pelvifemoral muscular dystrophy, progressive muscular dystrophy, scapulohumeral muscular dystrophy and Simmerlin's muscular dystrophy.

Additionally, since myostatin is highly homologous to GDF11, the myostatin peptides of the present invention will also find use in modulating GDF11 activity. See, e.g., NCBI Accession No. AF092734 for the sequence of GDF11.

Immunization can be achieved by any of the is methods known in the art including, but not limited to, use of peptide vaccines or DNA immunization. Such methods are described in detail below.

1. Myostatin PeTtides

Myostatin peptides for use with the present invention will generally include at least about 3 amino acids to about 200 amino acids, preferably at least about 3 amino acids to about 100 amino acids, more preferably at least about 3 to about 50 amino acids, even more preferably at least about 3 amino acids to about 30 amino acids, preferably about 3 to about 15 amino acids, and most preferably at least about 5 amino acids to about 25 amino acids or 5 to about 15 amino acids, from a selected myostatin protein. Representative myostatin proteins from 10 species from which the myostatin peptides of the present invention can be derived are shown in FIGS. 1A–1D. The amino acid sequence of bovine myostatin is also shown in FIG. 16B. The peptide will include at least one epitope which imparts immunogenicity to the myostatin molecule.

In preferred embodiments, the myostatin peptide is derived from the region of myostatin including but not limited to the region spanning amino acids 1 through 350, inclusive, of FIGS. 1A–1D (SEQ ID NOS:27–36); the region of myostatin spanning amino acids 1 through 275, inclusive, of FIGS. 1A–1D (SEQ ID NOS:27–36); the region of myostatin spanning amino acids 25 through 300, inclusive, of FIGS. 1A–1D (SEQ ID NOS:27–36); the region of myostatin spanning amino acids 50 through 325, inclusive, of FIGS. 1A–1D (SEQ ID NOS:27–36); the region of myostatin spanning amino acids 75 through 350, inclusive, of FIGS. 1A–1D (SEQ ID NOS:27–36); the region of myostatin spanning amino acids 45 through 376, inclusive, of FIGS. 1A–1D (SEQ ID NOS:27–36); 100 through 376, inclusive, of FIGS. 1A–1D (SEQ ID NOS:27–36); the region of myostatin spanning amino acids 235 through 376, inclusive, of FIGS. 1A–1D (SEQ ID NOS:27–36); or from any region believed to include an epitope of myostatin capable of eliciting an immune response in a subject to which the peptide is delivered.

Figure 17:
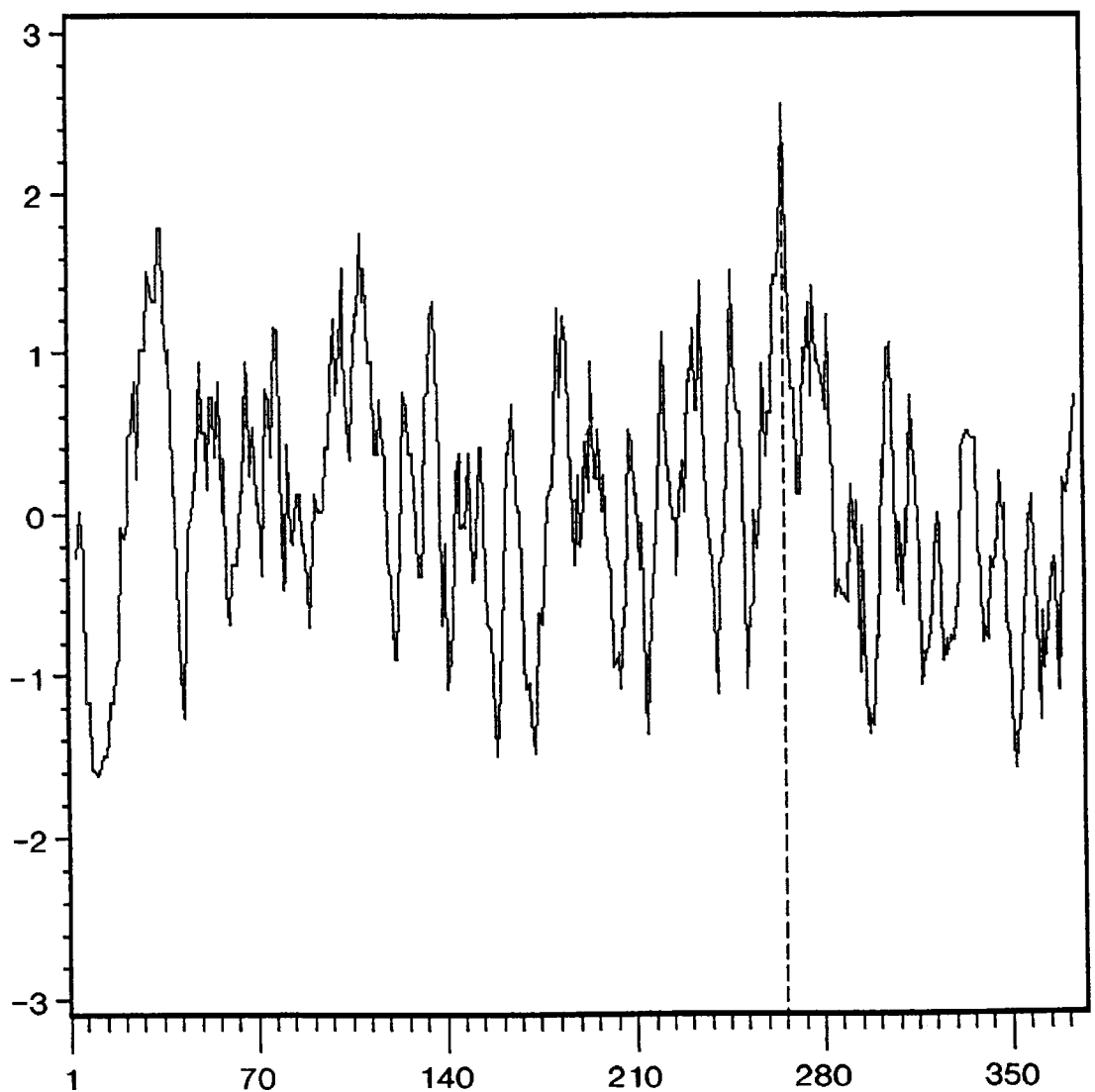
FIG. 17 shows a hydrophilicity profile of the myostatin protein. The profile was computed using an average group length of six amino acids. The three highest points of hydrophilicity are found at amino acid positions 263–268, which span the proteolytic cleavage site; positions 31–37; and positions 106–111.

In certain embodiments, myostatin peptides are derived from one of three regions of myostatin which display the highest points of hydrophilicity in the hydrophilicity profile shown in FIG. 17. The three highest points of hydrophilicity are found at amino acid positions 263–268, which spans the proteolytic cleavage site; positions 31–37; and positions 106–111. Thus, in these embodiments, the myostatin peptide comprises the amino acid sequence Lys-Arg-Ser-Arg-Arg-Asp (SEQ ID NO:37) which spans the proteolytic cleavage site; the amino acid sequence Lys-Glu-Asn-Val-Glu-Lys-Glu (SEQ ID NO:38) which corresponds to amino acids 31–37 of myostatin; or the amino acid sequence Ser-Leu-Lys-Asp-Asp-Asp (SEQ ID NO:39) which corresponds to amino acids 106 to 111 of myostatin.

In other embodiments, the myostatin peptide has at least about 75% amino acid identity to a peptide comprising the amino acid sequence of amino acids 3–18, inclusive of SEQ ID NO:4 (MYOS 1, shown in FIG. 2); amino acids 3–15, inclusive of SEQ ID NO:6 (MYOS 3, shown in FIG. 3); amino acids 3–17, inclusive, of SEQ ID NO:8 (MYOS 5, shown in FIG. 4); amino acids 3–16, inclusive of SEQ ID NO:10 (MYOS 7, shown in FIG. 5); amino acids 3–22, inclusive of SEQ ID NO:12 (MYOS 9, shown in FIG. 6); amino acids 3–25, inclusive of SEQ ID NO:14 (MYOS 11, shown in FIG. 7); amino acids 3–22, inclusive of SEQ ID NO:16 (MYOS 13, shown in FIG. 8); amino acids 3–19, inclusive, of SEQ ID NO:18 (MYOS 15, shown in FIG. 9); amino acids 3–18, inclusive, of SEQ ID NO:20 (MYOS 17, shown in FIG. 10); or amino acids 3–18, inclusive of SEQ ID NO:22 (MYOS 19, shown in FIG. 11). The positions of the various MYOS peptides above relative to full-length myostatin are shown in FIG. 12.

The myostatin peptide is optionally linked to an immunological carrier molecule in order to form a myostatin immunoconjugate, as described further below.

2. Myostatin Immunoconjugates

As explained above, myostatin is an endogenous molecule and, as such, it may be desirable to further increase the immunogenicity of the myostatin peptide (or multimers described below) by linking it to a carrier to form a myostatin immunoconjugate. This is especially necessary if the myostatin immunogen will be administered to the same species from which it is derived.

Suitable carriers are generally polypeptides which include antigenic regions of a protein derived from an infectious material such as a viral surface protein, or a carrier peptide sequence. These carriers serve to non-specifically stimulate T-helper cell activity and to help direct an immunogen of interest to antigen presenting cells (APCs) for processing and presentation at the cell surface in association with molecules of the major histocompatibility complex (MHC).

Several carrier systems have been developed for this purpose. For example, small peptide haptens are often coupled to protein carriers such as keyhole limpet hemocyanin (Bittle et al. (1982) *Nature* 298:30–33), bacterial toxins such as tetanus toxoid (Muller et al. (1982) *Proc. Natl. Acad. Sci. U.S.A.* 79:569–573), ovalbumin, leukotoxin polypeptides, and sperm whale myoglobin, to produce an immune response. These coupling reactions typically result in the incorporation of several moles of peptide hapten per mole of carrier protein.

Other suitable carriers for use with the present invention include VP6 polypeptides of rotaviruses, or functional fragments thereof, as disclosed in U.S. Pat. No. 5,071,651. Also useful is a fusion product of a viral protein and one or more epitopes from myostatin, which fusion products are made by the methods disclosed in U.S. Pat. No. 4,722,840. Still other suitable carriers include cells, such as lymphocytes, since presentation in this form mimics the natural mode of presentation in the subject, which gives rise to the immunized state. Alternatively, the myostatin immunogens may be coupled to erythrocytes, preferably the subject's own erythrocytes. Methods of coupling peptides to proteins or cells are known to those of skill in the art.

Delivery systems useful in the practice of the present invention may also utilize particulate carriers. For example, pre-formed particles have been used as platforms onto which immunogens can be coupled and incorporated. Systems based on proteosomes (Lowell et al. (1988) *Science* 240:800–802) and immune stimulatory complexes (Morein et al. (1984) *Nature* 308:457–460) are also known in the art.

Carrier systems using recombinantly produced chimeric proteins that self-assemble into particles may also be used with the present invention. For example, the yeast retrotransposon, Ty, encodes a series of proteins that assemble into virus like particles (Ty-VLPs; Kingsman et al. (1988) *Vaccines* 6:304–306). Thus, a gene, or fragment thereof, encoding the myostatin immunogen of interest may be inserted into the TyA gene and expressed in yeast as a fusion protein. The fusion protein retains the capacity to self assemble into particles of uniform size. Other useful virus-like carrier systems are based on HBsAg, (Valenzuela et al. (1985) *Bio/Technol.* 3:323–326; U.S. Pat. No. 4,722,840; Delpeyroux et al. (1986) *Science* 233:472–475), Hepatitis B core antigen (Clarke et al. (1988) *Vaccines* 88 (Ed. H. Ginsberg, et al.) pp. 127–131), Poliovirus (Burke et al. (1988) *Nature* 332:81–82), and Tobacco Mosaic Virus (Haynes et al. (1986) *Bio/Technol.* 4:637–641).

Especially preferred carriers include serum albumins, keyhole limpet hemocyanin, ovalbumin, sperm whale myoglobin, leukotoxin molecules as described above, and other proteins well known to those skilled in the art. One particular leukotoxin polypeptide, for use as a carrier herein, is shown in FIGS. 15A–15D. Myostatin is conveniently inserted into the BamH1 site present at nucleotide position 3334, as described further in the examples.

Protein carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptide immunogens.

Carriers can be physically conjugated to the myostatin immunogen of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for a selected myostatin immunogen.

The myostatin immunogens can also be administered via a carrier virus which expresses the same. Carrier viruses which will find use herein include, but are not limited to, the vaccinia and other pox viruses, adenovirus, and herpes virus. By way of example, vaccinia virus recombinants expressing the proteins can be constructed as follows. The DNA encoding a particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the desired immunogen into the viral genome. The resulting TK-recombinant can be selected by culturing the cells in the presence of 5-bromodeoxyuridine and picking viral plaques resistant thereto.

3. Myostatin Multimers

Immunogenicity of the myostatin immunogens may also be significantly increased by producing immunogenic forms of the molecules that comprise multiple copies of selected epitopes. In this way, endogenous myostatin may be rendered an effective autoantigen.

Accordingly, in one aspect of the invention, vaccine compositions containing myostatin multimers are provided in either nucleic acid or peptide form for delivery to a subject. The myostatin multimer will have more than one copy of selected myostatin immunogens, peptides or epitopes, as described above, or multiple tandem repeats of a selected myostatin immunogen, peptide or epitope. Thus, the myostatin multimers may comprise either multiple or tandem repeats of selected myostatin sequences, multiple or tandem repeats of selected myostatin epitopes, or any conceivable combination thereof. Myostatin epitopes may be identified using techniques as described in detail above.

For example, the myostatin multimer may correspond to a molecule with repeating units of the general formula (MP-X-MP)y wherein MP is a myostatin peptide, X is selected from the group consisting of a peptide linkage, an amino acid spacer group and $[MP]_n$, where n is greater than or equal to 1, y is greater than or equal to 1, and further wherein "MP" may comprise any MP peptide. Thus, the myostatin multimer may contain from 2–64 or more myostatin peptides, more preferably 2–32 or 2–16 myostatin peptides.

Further, the selected myostatin immunogen sequences may all be the same, or may correspond to different derivatives, analogs, variants or epitopes of myostatin so long as they retain the ability to elicit an immune response. Additionally, if the myostatin immunogens are linked either chemically or recombinantly to a carrier, myostatin peptides may be linked to either the 5'-end, the 3'-end, or may flank the carrier in question. Further, the myostatin multimer may be located at sites internal to the carrier.

One particular carrier for use with the present myostatin multimers is a leukotoxin polypeptide as described above. For example, myostatin oligo repeats can be conveniently inserted into the BamH1 site present at nucleotide position 3334 of the leukotoxin polypeptide shown in FIGS. 15A–15D.

As explained above, spacer sequences may be present between the myostatin moieties. For example, Arg-Ser and Gly-Ser dimers are present in the MYOS peptides exemplified herein which provide spacers between repeating sequences of the myostatin peptides. The strategic placement of various spacer sequences between selected myostatin immunogens can be used to confer increased immunogenicity on the subject constructs. Accordingly, under the invention, a selected spacer sequence may encode a wide variety of moieties such as a single amino acid linker or a sequence of two to several amino acids. Selected spacer groups may preferably provide enzyme cleavage sites so that the expressed multimer can be processed by proteolytic enzymes in vivo (by APCs, or the like) to yield a number of peptides, each of which contain at least one T-cell epitope derived from the carrier portion, and which are preferably fused to a substantially complete myostatin peptide sequence.

The spacer groups may be constructed so that the junction region between selected myostatin moieties comprises a clearly foreign sequence to the immunized subject, thereby conferring enhanced immunogenicity upon the associated myostatin peptides. Additionally, spacer sequences may be constructed so as to provide T-cell antigenicity, such as those sequences which encode amphipathic and/or α-helical peptide sequences which are generally recognized in the art as providing immunogenic helper T-cell epitopes. The choice of particular T-cell epitopes to be provided by such spacer sequences may vary depending on the particular vertebrate species to be vaccinated. Although particular myostatin portions are exemplified which include spacer sequences, it is also an object of the invention to provide one or more myostatin multimers comprising directly adjacent myostatin sequences (without intervening spacer sequences).

The myostatin multimeric sequence thus produced renders a highly immunogenic myostatin antigen for use in the compositions of the invention.

The myostatin peptides, immunoconjugates and is multimers can be produced using the methods described below, and used for nucleic acid immunization, gene therapy, protein-based immunization methods, and the like.

4. Nucleic Acid-Based Immunization Methods

Generally, nucleic acid-based vaccines for use with the present invention will include relevant regions encoding a myostatin immunogen, with suitable control sequences and, optionally, ancillary therapeutic nucleotide sequences. The nucleic acid molecules are prepared in the form of vectors which include the necessary elements to direct transcription and translation in a recipient cell.

In order to augment an immune response in an immunized subject, the nucleic acid molecules can be administered in conjunction with ancillary substances, such as pharmacological agents, adjuvants, or in conjunction with delivery of vectors encoding biological response modifiers such as cytokines and the like. Other ancillary substances include, but are not limited to, substances to increase weight gain, muscle mass or muscle strength, such as growth hormones, growth promoting agents, beta antagonists, partitioning agents and antibiotics.

Nucleotide sequences selected for use in the present invention can be derived from known sources, for example, by isolating the same from cells or tissue containing a desired gene or nucleotide sequence using standard techniques, or by using recombinant or synthetic techniques.

Once coding sequences for the myostatin immunogens have been prepared or isolated, such sequences can be cloned into any suitable vector or replicon. Numerous cloning vectors are known to those of skill in the art, and the selection of an appropriate cloning vector is a matter of choice. Ligations to other sequences, e.g., ancillary molecules or carrier molecules, are performed using standard procedures, known in the art. One or more myostatin immunogen portions of the chimera can be fused 5' and/or 3' to a desired ancillary sequence or carrier molecule. Alternatively, one or more myostatin immunogen portions may be located at sites internal to the carrier molecule, or such portions can be positioned at both terminal and internal locations in the chimera.

Alternatively, DNA sequences encoding the myostatin immunogens of interest, optionally linked to carrier molecules, can be prepared synthetically rather than cloned. The DNA sequences can be designed with appropriate codons for the particular sequence. The complete sequence of the immunogen is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

The coding sequence is then placed under the control of suitable control elements for expression in suitable host tissue in vivo. The choice of control elements will depend on the subject being treated and the type of preparation used. Thus, if the subject's endogenous transcription and translation machinery will be used to express the immunogens, control elements compatible with the particular subject will be utilized. In this regard, several promoters for use in mammalian systems are known in the art. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression.

Typically, transcription termination and polyadenylation sequences will also be present, located 3'to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the constructs for use with the present invention.

Enhancer elements may also be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence.

Once prepared, the nucleic acid vaccine compositions can be delivered to the subject using known methods. In this regard, various techniques for immunization with antigen-encoding DNAs have been described. See, e.g., U.S. Pat. No. 5,589,466 to Feigner et al.; Tang et al. (1992) *Nature* 358:152; Davis et al. (1993) *Hum. Molec. Genet.* 2:1847; Ulmer et al. (1993) *Science* 258:1745; Wang et al. (1993) *Proc. Natl. Acad. Sci. USA* 90:4156; Eisenbraun et al. (1993) *DNA Cell Biol.* 12:791; Fynan et al. (1993) *Proc. Natl. Acad. Sci. USA* 90:12476; Fuller et al. (1994) *AIDS Res. Human Retrovir.* 10:1433; and Raz et al. (1994) *Proc. Natl. Acad. Sci. USA* 91:9519. General methods for delivering nucleic acid molecules to cells in vitro, for the subsequent reintroduction into the host, can also be used, such as liposome-mediated gene transfer. See, e.g., Hazinski et al. (1991) *Am. J. Respir. Cell Mol. Biol.* 4:206–209; Brigham et al. (1989) *Am. J. Med. Sci.* 298:278–281; Canonico et al. (1991) *Clin. Res.* 39:219A; and Nabel et al. (1990) *Science* 249:1285–1288. Thus, the nucleic acid vaccine compositions can be delivered in either liquid or particulate form using a variety of known techniques. Typical vaccine compositions are described more fully below.

5. Protein-Based Immunization Methods

Peptide-based vaccine compositions can also be produced using a variety of methods known to those skilled in the art. In particular, myostatin immunogens can be isolated directly from native sources, using standard purification techniques. Alternatively, the immunogens can be recombinantly produced using the nucleic acid expression systems described above, and purified using known techniques. Peptide immunogens can also be synthesized, based on described amino acid sequences or amino acid sequences derived from the DNA sequence of a molecule of interest, using chemical polymer syntheses such as solid phase peptide synthesis. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Peptide immunogens may also be produced by cloning the coding sequences therefor into any suitable expression vector or replicon. Numerous cloning vectors are known to those of skill in the art, and the selection of an appropriate cloning vector is a matter of choice. Examples of recombinant DNA vectors for cloning, and host cells which they can transform, include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomiyces), YCp19 (Saccharomyces) and bovine papilloma virus (mammalian cells). See, generally, *DNA Cloning*: Vols. I & II, supra; Sambrook et al., supra; B. Perbal, supra.

For example, the coding sequence for myostatin from a number of vertebrate species, including mouse, rat, human, baboon, cattle, pig, sheep, chicken and turkey has been determined. See, e.g., U.S. Pat. No. 5,827,733 and NCBI Accession No. U84OC5 for the nucleotide sequence of murine myostatin; U.S. Pat. No. 5,827,733, International Publication No. WO 98/33887, and NCBI Accession No. AF019627 for the nucleotide sequence of human myostatin; FIG. 16A herein, as well as International Publication Nos. WO 99/02667 and WO 98/33887, and NCBI Accession No. AFO19620 for the nucleotide sequence of bovine myostatin; NCBI Accession No. AFO19626 for the nucleotide sequence of zebrafish myostatin; International Publication No. WO 98/33887, for the nucleotide sequences of rat (see, also NCBI Accession No. AFO19624), baboon (see, also NCBI Accession No. AFO19619), porcine (see, also NCBI Accession No. AFO19623), ovine (see, also NCBI Accession No. AFO19622), chicken (see, also NCBI Accession No. AFO19621) and turkey (seem also NCBI Accession No. AFO19625) myostatin. The myostatin sequence is highly conserved across all of these species.

Portions of these sequences encoding desired myostatin peptides, and if desired, a sequence encoding a carrier protein, can be cloned, isolated and ligated together using recombinant techniques generally known in the art. See, e.g., Sambrook et al., supra.

The gene can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence. The peptide immunogens can be expressed using, for example, the E. coli tac promoter or the protein A gene (spa) promoter and signal sequence. Leader sequences can be removed by the bacterial host in post-translational processing. See, e.g., U.S. Pat. Nos. 4,431,739; 4,425,437; 4,338,397. Ancillary sequences, such as those described above, may also be present.

In addition to control sequences, it may be desirable to add regulatory sequences which allow for regulation of the expression of the immunogen sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular myostatin immunogen may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the immunogen from the host organism, with subsequent cleavage of the secretory signal. It may also be desirable to produce mutants or analog of the immunogen. Mutants or analogs may be prepared by the deletion of a portion of the sequence encoding the immunogen, or if present, a portion of the sequence encoding the desired carrier molecule, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; *DNA Cloning*, Vols. I and II, supra; *Nucleic Acid Hybridization*, supra; Kunkel, T. A. *Proc. Natl. Acad. Sci. USA* (1985) 82:448; Geisselsoder et al. *BioTechniques* (1987) 5:786; Zoller and Smith, *Methods Enzymol.* (1983) 100:468; Dalbie-McFarland et al. *Proc. Natl. Acad. Sci USA* (1982) 79:6409.

The myostatin immunogens can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli*, *Bacillus subtilis*, and *Streptococcus spp*., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the myostatin immunogens are produced by growing host cells transformed by an expression vector described above under conditions whereby the immunogen is expressed. The expressed immunogen is then isolated from the host cells and purified. If the expression system secretes the immunogen into growth media, the product can be purified directly from the media. If it is not secreted, it can be isolated from cell lysates. The selection of the appropriate growth conditions and recovery methods are within the skill of the art.

Once obtained, the myostatin peptides, with or without associated carrier, may be formulated into vaccine compositions, such as vaccine compositions as described further below, in order to elicit antibody production in a subject vertebrate.

6. Antibody Production

The subject myostatin peptides can be used to generate antibodies for use in passive immunization methods or for immunopurification or immunodiagnostic purposes. Typically, peptides useful for producing antibodies will usually be at least about 3–5 amino acids in length, preferably 7–10 amino acids in length, and most preferably at least about 10 to 15 amino acids in length, or more.

Antibodies against the subject immunogens include polyclonal and monoclonal antibody preparations, monospecific antisera, as well as preparations including hybrid antibodies, altered antibodies, $F(ab')_2$ fragments, F(ab) fragments, $F_v$ fragments, single domain antibodies, chimeric antibodies, humanized antibodies, and functional fragments thereof, which retain specificity for the target molecule in question. For example, an antibody can include variable regions, or fragments of variable regions, which retain specificity for the molecule in question. The remainder of the antibody can be derived from the species in which the antibody will be used. Thus, if the antibody is to be used in a human, the antibody can be "humanized" in order to reduce immunogenicity yet retain activity. For a description of chimeric antibodies, see, e.g., Winter, G. and Milstein, C. (1991) *Nature* 349:293–299; Jones, P. T. et al. (1986) *Nature* 321:522–525; Riechmann, L. et al. (1988) 332:323–327; and Carter, P. et al. (1992) *Proc. Natl. Acad. Sci. USA* 89:4285–4289. Such chimeric antibodies may contain not only combining sites for the target molecule, but also binding sites for other proteins. In this way, bifunctional reagents can be generated with targeted specificity to both external and internal antigens.

If polyclonal antibodies are desired, a selected mammal, (e.g., mouse, rabbit, goat, horse, etc.) is immunized with the desired antigen, or its fragment, or a mutated antigen, as described above. Prior to immunization, it may be desirable to further increase the immunogenicity of a particular immunogen. This can be accomplished in any one of several ways known to those of skill in the art.

For example, immunization for the production of antibodies is generally performed by mixing or emulsifying the protein in a suitable excipient, such as saline, preferably in an adjuvant such as Freund's complete adjuvant, or any of the adjuvants described below, and injecting the mixture or emulsion parenterally (generally subcutaneously or intramuscularly). The animal is generally boosted 2–6 weeks later with one or more injections of the protein in saline, preferably using Freund's incomplete adjuvant, or the like. Antibodies may also be generated by in vitro immunization, using methods known in the art. Polyclonal antisera is then obtained from the immunized animal and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies are generally prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice). See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the myostatin peptide of interest, or fragment thereof, can be screened for various properties; i.e., for isotype, epitope, affinity, etc.

Functional fragments of the antibodies can also be made against the myostatin peptide of interest and can be produced by cleaving a constant region, not responsible for antigen binding, from the antibody molecule, using e.g., pepsin, to produce $F(ab')_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques. These fragments are known as $F_v$.

Chimeric or humanized antibodies can also be produced using the subject immunogens. These antibodies can be designed to minimize unwanted immunological reactions attributable to heterologous constant and species-specific framework variable regions typically present in monoclonal and polyclonal antibodies. For example, if the antibodies are to be used in human subjects, chimeric antibodies can be created by replacing non-human constant regions, in either the heavy and light chains, or both, with human constant regions, using techniques generally known in the art. See, e.g., Winter, G. and Milstein, C. (1991) *Nature* 349:293–299; Jones, P. T. et al. (1986) *Nature* 321:522–525; Riechmann, L. et al. (1988) 332:323–327; and Carter, P. et al. (1992) *Proc. Natl. Acad. Sci. USA* 89:4285–4289.

7. Vaccine Compositions

Once the above molecules are produced, they are formulated into vaccine compositions for delivery to a vertebrate subject. The relevant myostatin molecule is administered alone, or mixed with a pharmaceutically acceptable vehicle or excipient. Suitable vehicles are, for example, water, saline, dextrose, glycerol, ethanol, or the like, and combinations thereof. In addition, the vehicle may contain minor amounts of auxiliary substances such as wetting or emulsifying agents, pH buffering agents, or adjuvants which enhance the effectiveness of the vaccine. Suitable adjuvants are-described further below. Actual methods of preparing such dosage forms are known, or will be apparent, to those skilled in the art. See, e.g., *Remington's Pharmaceutical Sciences*, Mack Publishing Company, Easton, Pa., 18th edition, 1990. The composition or formulation to be administered will contain a quantity of the myostatin immunogen adequate to achieve the desired immunized state in the subject being treated.

As explained above, the vaccine compositions of the present invention may include adjuvants to further increase the immunogenicity of the myostatin immunogen. Adjuvants may include for example, emulsifiers, muramyl dipeptides, avridine, aluminum hydroxide, oils, saponins and other substances known in the art. For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. In this regard, a "mineral oil" is defined herein as a mixture of liquid hydrocarbons obtained from petrolatum via a distillation technique; the term is synonymous with "liquid paraffin," "liquid petrolatum" and "white mineral oil." The term is also intended to include "light mineral oil," i.e., an oil which is similarly obtained by distillation of petrolatum, but which has a slightly lower specific gravity than white mineral oil. See, e.g., *Remington's Pharmaceutical Sciences*, supra. A particularly preferred oil component is the oil-in-water emulsion sold under the trade name of EMULSIGEN PLUS™ (comprising a light mineral oil as well as 0.05% formalin, and 30 mcg/mL gentamicin as preservatives), available from MVP Laboratories, Ralston, Nebr., or the VSA-3 adjuvant which is a modified form of the EMULSIGEN PLUS™ adjuvant. Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines and thiouroniums (Gall, D. (1966) *Immunology* 11:369–386). Specific compounds include dimethyldioctadecylammonium bromide (DDA) (available from Kodak) and N,N-dioctadecyl-N,N-bis(2-hydroxyethyl) propanediamine ("avridine"). The use of DDA as an immunologic adjuvant has been described; see, e.g., the Kodak Laboratory Chemicals Bulletin 56(1):1–5 (1986); *Adv. Drug Deliv. Rev.* 5(3):163–187 (1990); *J. Controlled Release* 7:123–132 (1988); *Clin. Exp. Immunol.* 78(2):256–262 (1989); *J. Immunol. Methods* 97(2):159–164 (1987); *Immunology* 58(2):245–250 (1986); and *Int. Arch. Allergy Appl. Immunol.* 68(3):201–208 (1982). Avridine is also a well-known adjuvant. See, e.g., U.S. Pat. No. 4,310,550 to Wolff, III et al., which describes the use of N,N-higher alkyl-N', N'-bis(2-hydroxyethyl)propane diamines in general, and avridine in particular, as vaccine adjuvants. U.S. Pat. No.

5,151,267 to Babiuk, and Babiuk et al. (1986) *Virology* 159:57–66, also relate to the use of avridine as a vaccine adjuvant.

The vaccine compositions of the present invention can also include ancillary substances, such as pharmacological agents, cytokines, or other biological response modifiers. Other ancillary substances include, but are not limited to, substances to increase weight gain, muscle mass or muscle strength, such as growth hormones, growth promoting agents, beta antagonists, partitioning agents and antibiotics.

The vaccines of the present invention are normally prepared as injectables, either as liquid solutions or suspensions, or as solid forms which are suitable for solution or suspension in liquid vehicles prior to injection. The preparation may also be emulsified or the active ingredient encapsulated in liposome vehicles or other particulate carriers used.

The vaccine compositions may also be prepared in solid form. For example, solid particulate formulations can be prepared for delivery from commercially available needleless injector devices. Alternatively, solid dose implants can be provided for implantation into a subject. Controlled or sustained release formulations may also be used and are made by incorporating the myostatin immunogens into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures.

Furthermore, the immunogens may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition is formulated to contain an effective amount of the myostatin immunogen, the exact amount being readily determined by one skilled in the art, wherein the amount depends on the animal to be treated, the capacity of the animal's immune system to synthesize antibodies, and the degree of immunoneutralization of myostatin desired. For purposes of the present invention, vaccine formulations including approximately 1 $\mu$g to about 1 mg, more generally about 5 $\mu$g to about 200 $\mu$g of immunogen per dose of injected solution should be adequate to raise an immunological response when administered. If a peptide-carrier chimera is used, the ratio of immunogen to carrier in the vaccine formulation will vary based on the particular carrier and immunogen selected to construct such molecules. Effective dosages can be readily established by one of ordinary skill in the art through routine trials establishing dose response curves.

The subject is immunized by administration of one of the above-described vaccine compositions in at least one dose, and preferably two or more doses. Moreover, the animal may be administered as many doses as is required to maintain a state of immunity.

Any suitable pharmaceutical delivery means may be employed to deliver the vaccine composition to the vertebrate subject. For example, conventional needle syringes, spring or compressed gas (air) injectors (U.S. Pat. No. 1,605,763 to Smoot; U.S. Pat. No. 3,788,315 to Laurens; U.S. Pat. No. 3,853,125 to Clark et al.; U.S. Pat. No. 4,596,556 to Morrow et al.; and U.S. Pat. No. 5,062,830 to Dunlap), liquid jet injectors (U.S. Pat. Nos. 2,754,818 to Scherer; U.S. Pat. No. 3,330,276 to Gordon; and U.S. Pat. No. 4,518,385 to Lindmayer et al.), and particle injectors (U.S. Pat. Nos. 5,149,655 to McCabe et al. and U.S. Pat. No. 5,204,253 to Sanford et al.) are all appropriate for delivery of the vaccine compositions.

Preferably, the vaccine composition is administered intramuscularly, subcutaneously, intravenously, subdermally, or intradermally, to the subject. If a jet injector is used, a single jet of the liquid vaccine composition is ejected under high pressure and velocity, e.g., 1200–1400 PSI, thereby creating an opening in the skin and penetrating to depths suitable for immunization.

Below are examples of specific embodiments for carrying out the present invention. The examples are offered for illustrative purposes only, and are not intended to limit the scope of the present invention in any way.

C. Experimental

EXAMPLE 1

Identification of Immunogenic Myostatin Pestides

A number of regions of the bovine myostatin molecule were identified as potentially immunogenic based on computer analysis of the full-length molecule using various computer programs. One program used formulates hydropathy scales from the amino acid sequence of the protein based on the hydrophobic and hydrophilic properties of each of the 20 amino acids. Hopp and Woods, *Proc. Natl. Acad. Sci. USA* (1981) 78:3824–3828. FIG. 17 depicts a hydrophilicity profile computed using an average group length of six amino acids. The three highest points of hydrophilicity of the myostatin molecule were found at amino acid positions 263–268, which spans the proteolytic cleavage site and has the amino acid sequence Lys-Arg-Ser-Arg-Arg-Asp (SEQ ID NO:37); positions 31–37 which has the amino acid sequence Lys-Glu-Asn-Val-Glu-Lys-Glu (SEQ ID NO:38); and positions 106–111 which has the amino acid sequence Ser-Leu-Lys-Asp-Asp-Asp (SEQ ID NO:39).

Analysis of the protein was also done using the program PC/Gene, Release 6.60 (Intelligenetics Inc., Geneva, Switzerland). Three-dimensional analysis of the myostatin protein was conducted using the Swiss-Pdb Viewer v2.6 (http://expasy.hcuge.ch/spdbv/mainpage.html).

From this information, a series of representative DNA oligomers were designed and constructed with a Beckman Oligo 1000M DNA Synthesizer using phosphoramidite chemistry. The oligomers were termed MYOS 1–20. Myos 1, 3, 5, 7, 9, 11, 13, 15, 17 and 19 (shown in FIGS. 2 through 11, respectively) include portions of the coding stand of DNA while MYOS 2, 4, 6, 8, 10, 12, 14, 16, 18 and 20 include portions of the complimentary strand. The position of these peptides with reference to the full-length myostatin molecule is shown in FIG. 12.

The DNA oligomers coded for peptides with 12 to 23 amino acids, flanked by 2 amino acid linkers for linkage to a carrier molecule (see further below). These peptides collectively represented the entire active portion of the protein, as well as three individual sections upstream of the proteolytic cleavage site which releases the active protein.

In particular, based on computer analysis, three portions of the active protein were selected as primary immunizing targets. The first portion was prepared by combining the oligonucleotide pair designated MYOS 1 and 2 and contained the proteolytic cleavage site and N-terminus of the active protein. MYOS 1 gave the highest antigenic determinant rating using the Hopp and Woods computer program (see FIG. 17). Three-dimensional analysis of the active portion of myostatin showed that the MYOS 1 peptide is exposed on the protein surface and is therefore likely to be seen by the immune system. MYOS 1 also overlaps the proteolytic cleavage site, which releases the active portion of the protein. Blocking this site using antibodies thereto prevents cleavage of the protein and release of the active portion of the protein to prevent its effect on muscle tissue.

Two other segments of the active protein (MYOS 5 and 6 and MYOS 9 and 10) were selected because they appeared to form a loop and a helix based on a three-dimensional structural analysis. This loop structure is likely exposed on the protein surface and therefore able to be seen by the immune system. Antibodies generated to these portions of the molecule likely bind myostatin protein and remove it from circulation. The remainder of the active portion of the protein was reconstructed from the oligonucleotide pairs (MYOS 3 and 4, MYOS 7 and 8, MYOS 11 and 12, MYOS 13 and 14). Use of the entire active portion assures the proper three-dimensional structure to elicit an effective immune response. One of the regions upstream of the active portion of the protein, (MYOS 15 and 16) was selected based on computer analysis of likely antigenic epitopes. The other two upstream portions of the protein were selected to contain the proteolytic cleavage site (MYOS 19 and 20, which contain the cleavage site and amino acids immediately upstream of the cleavage site) or to be close to it (MYOS 17 and 18) so an antibody which binds to the site would interfere with the protease activity.

Based on comparisons with other known protein sequences, myostatin has areas of homology with other transforming growth factor β proteins. Bone morphogenetic protein 6 (BMP-6) has a great deal of homology to the middle and C-terminus regions of the active portion of myostatin.

EXAMPLE 2

Construction of pCB150

The oligomers above were designed to be fused to the 3'-terminus of a polynucleotide encoding a 52 kDa leukotoxin (LKT) carrier protein, termed "LKT 114" herein. This polynucleotide was derived from the lkta gene present in plasmid pCB114, described in U.S. Pat. No. 5,837,268. This plasmid, the nucleotide sequence of this gene and the corresponding amino acid sequence are shown in FIGS. 15A–15D herein and also described in U.S. Pat. No. 5,837, 268, incorporated herein by reference in its entirety. The gene encodes a shortened version of leukotoxin which was developed from the recombinant leukotoxin gene present in plasmid pAA352 (ATCC Accession No. 68283 and described in U.S. Pat. No. 5,476,657, incorporated herein by reference in its entirety) by removal of an internal DNA fragment of approximately 1300 bp in length. The LKT 114 polypeptide has an estimated molecular weight of 52 kDa and contains convenient restriction sites for use in producing the fusion proteins of the present invention.

Plasmid pCB150, containing the coding sequence for LKT 114, into which the MYOS oligonucleotides were cloned, was prepared as follows. The leukotoxin gene was isolated as described in U.S. Pat. Nos. 5,476,657 and 5,837, 268, incorporated herein by reference in their entireties. In particular, to isolate the leukotoxin gene, gene libraries of P. haemolytica A1 (strain B122) were constructed using standard techniques. See, Lo et al., Infect. Immun., supra; DNA CLONING: Vols. I and II, supra; and Sambrook et al., supra. A genomic library was constructed in the plasmid vector pUC13 and a DNA library constructed in the bacteriophage lambda gt11. The resulting clones were used to transform E. coli and individual colonies were pooled and screened for reaction with serum from a calf which had survived a P. haemolytica infection and that had been boosted with a concentrated culture supernatant of P. haemolytica to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See, Lo et al., Infect. Immun., supra. To confirm this, smaller fragments were re-cloned and the restriction maps compared. It was determined that approximately 4 kilobase pairs of DNA had been cloned. Progressively larger clones were isolated by carrying out a chromosome walk (5'to 3'direction) in order to isolate full-length recombinants which were approximately 8 kb in length. The final construct was termed pAA114. This construct contained the entire leukotoxin gene sequence.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432: lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3'end of the lktA gene (StyI BamHI fragment from pAA345) was ligated to StyI BamHI-digested pAA342, yielding the plasmid pAA352. The P. haemolytica leukotoxin produced from the pAA352 construct is hereinafter referred to as LKT 352.

Plasmid pAA352 was then used to prepare a shortened version of the recombinant leukotoxin polypeptide. The shortened LKT gene was produced by deleting an internal DNA fragment of approximately 1300 bp in length from the recombinant LKT gene as follows. The plasmid pCB113, (ATCC Accession No. 69749 and described in U.S. Pat. No. 5,837,268, incorporated herein by reference in its entirety) which includes the LKT 352 polypeptide, was digested with the restriction enzyme BstBI (New England Biolabs). The resultant linearized plasmid was then digested with mung-bean nuclease (Pharmacia) to remove the single stranded protruding termini produced by the BstBI digestion. The blunted DNA was then digested with the restriction enzyme NaeI (New England Biolabs), and the digested DNA was loaded onto a 1% agarose gel where the DNA fragments were separated by electrophoresis. A large DNA fragment of approximately 6190 bp was isolated and purified from the agarose gel using a Gene Clean kit (Bio 101), and the purified fragment was allowed to ligate to itself using bacteriophage T4 DNA ligase (Pharmacia). The resulting ligation mix was used to transform competent E. coli JM105 cells, and positive clones were identified by their ability to produce an aggregate protein having an appropriate molecular weight. The recombinant plasmid thus formed was designated pCB114, (described in U.S. Pat. No. 5,837,268, incorporated herein by reference in its entirety), and produces a shortened leukotoxin polypeptide termed "LKT 114".

Plasmid pCB114 was then used to produce plasmid pSLKT-30. Plasmid pSLKT-30 was made by cloning the leukotoxin-encoding fragment from pCB114 by PCR into plasmid pAA352 (ATCC Accession No. 68283 and described in U.S. Pat. No. 5,476,657, incorporated herein by reference in its entirety). In doing so, mutations were introduced near the C-terminus, resulting in two amino acid changes to the native leukotoxin molecule. Thus, a PCR fragment of the affected area was cloned back into plasmid PSLKT-30. Specifically, a fragment from pSLKT-30 was created by PCR using LKT6 (SEQ ID NO:40) as the upstream PCR primer, and LKT13 (SEQ ID NO:41) as the downstream PCR primer:

LKT6: TTA GAG AGT TAT GCC GAA CGC (SEQ ID NO:40);

LKT13: GAT GCC ATC GCT AGC TAG CTA GGA TCC CCT AGC AAA TTC AAG AGA AGA TAA ACT TTG ATC CAA CAT TGA (SEQ ID NO:41).

The fragment contained the desired change and the NsiI and NcoI restriction sites. The isolated fragment was digested using the restriction enzymes NsiI and NcoI, as was the plasmid pSLKT-30. The NsiI/NcoI fragment was removed from the plasmid and replaced with the PCR fragment, resulting in the mutation back to the original sequence. The plasmid was termed pCB150. A diagram of plasmid pCB150 is shown in FIG. 14. The nucleic acid sequence of LKT 114 from plasmid pCB150 is shown in FIGS. 15A–15D.

EXAMPLE 3

Construction of LKT-Myostatin Peptide Multimer Fusions

Multiple copies of each oligomer pair described in Example 1 were used to prepare tandem repeats of coding sequences for myostatin peptide multimers joined to the LKT 114 gene. The entire active portion of the protein was also reconstructed and fused to LKT 114 for use as an immunizing agent.

Representative LKT-myostatin peptide fusions were constructed as follows. Oligonucleotide pairs from Example 1 were annealed and ligated into the vector pUC19 (Pharmacia) which had been digested with the restriction endonuclease HincII. The ligated DNA was used to transform *E. coli* strain TOP10F' (Invitrogen). Transformants containing the oligonucleotide inserts were identified by PCR and restriction endonuclease mapping.

The oligonucleotide pairs were designed to be linked together by ligating the BaRHI site at the front end of one oligonucleotide pair to the BglII site at the back end of a second copy of the oligonucleotide pair. The restriction sites at the point of ligation were disabled leaving a single BamHI site at the front end of the repeat and a single BglII site at the back end of the repeat. Tandem repeats of each oligonucleotide pair were constructed by digesting the oligonucleotide-containing plasmid with the restriction endonucleases BamHI and BglII to release the inserted oligonucleotide fragment. This fragment was then ligated back into the oligonucleotide-containing plasmid, which had been digested with the restriction endonuclease BglII. The ligated DNA was used to transform *E. coli* strain TOP10F'. Transformants containing repeats of the oligonucleotide inserts were identified by PCR and restriction endonuclease mapping. This process was repeated until pUC19 plasmids containing at least four repeating copies and up to 8 copies of each oligonucleotide pair in the correct orientation were produced.

In addition to being linked to themselves, some of the oligonucleotide pairs were also designed to link to each other to recreate the active region of the myostatin protein as closely as possible. This was done by ligating BamHI, BglII cut oligonucleotide pair MYOS 3/4 in to the BglII site behind oligonucleotide pair MYOS 1/2 in the pUC19 vector. This was followed by ligating in oligonucleotide pair MYOS 5/6 cut with BstBI and BglII into the vector containing the reconstructed myostatin active region cut with BstBI and BglII. Oligonucleotide pair MYOS 7/8 was cut with BamHI and BglII and ligated into the vector containing the reconstructed myostatin active region at the BglII site. Oligonucleotide pair MYOS 9/10 containing vector was cut with EcoRI and the EcoRI fragment from the pUC19 myostatin reconstruction was ligated in. Oligonucleotide pair MYOS 11/12 was cut with BamHI and BglII and ligated into the vector containing the reconstructed myostatin active region at the BglII site. This was followed by ligating in oligonucleotide pair MYOS 13/14 cut with BsmI and BglII into the vector containing the reconstructed myostatin active region cut with BsmI and BglII. This completed the reconstruction of the coding sequence for the myostatin active region, which contained three sets of two amino acid linkers inserted into the myostatin active region sequence at positions 55–60, 139–144 and 241–246 and at the C-terminus (see FIG. 13).

The multiple copies of each oligonucleotide pair and the myostatin active region reconstruction were then released from the pUC19 plasmid by digestion with the restriction endonucleases BamHI and BglII. These DNA fragments were then ligated into the plasmid pCB150. Plasmid pCB150 was digested with the restriction endonuclease BamHI. The ligated DNA was used to transform *E. coli* strain TOP10F'. Transformants containing the oligonucleotide inserts were identified by PCR and restriction endonuclease mapping. The recombinant plasmids were designated pJS121, pJS122, pJS123, pJS124, pJS125, pJS126, pJS127, pJS128, pJS129, pJS130, and pCB317.

The plasmid pJS121 contains 6 repeating copies of oligonucleotide pair MYOS 1/2 fused to LKT 114. The plasmid pJS122 contains 8 repeating copies of oligonucleotide pair MYOS 3/4 fused to LKT 114. The plasmid pJS123 contains 8 repeating copies of oligonucleotide pair MYOS 5/6 fused to LKT 114. The plasmid pJS124 contains 8 repeating copies of oligonucleotide pair MYOS 7/8 fused to LKT 114. The plasmid pJS125 contains 6 repeating copies of oligonucleotide pair MYOS 9/10 fused to LKT 114. The plasmid pJS126 contains 4 repeating copies of oligonucleotide pair MYOS 11/12 fused to LKT 114. The plasmid pJS127 contains 6 repeating copies of oligonucleotide pair MYOS 13/14 fused to LKT 114. The plasmid pJS128 contains 4 repeating copies of oligonucleotide pair MYOS 15/16 fused to LKT 114. The plasmid pJS129 contains 8 repeating copies of oligonucleotide pair MYOS 17/18 fused to LKT 114. The plasmid pJS130 contains 4 repeating copies of oligonucleotide pair MYOS 19/20 fused to LKT 114. The plasmid pCB317 contains a single copy of the myostatin active region reconstruction fused to LKT 114.

EXAMPLE 4

Purification of LKT-Myostatin Peptide Fusions

The recombinant LKT-myostatin peptide fusion proteins from above were expressed as inclusion bodies and purified using the following procedure. A loop of cells from each frozen stock was inoculated into 10 ml of TB broth in a 50 ml Erlenmeyer flask. The TB broth was supplemented with 100 μg/ml of ampicillin and incubated at 37° C. for 12–16 hours on an Innova 4000 shaker at 250 rpm. The culture was used to inoculate one liter of TB broth in a 4L Erlenmeyer flask. The TB broth was supplemented with 100 μg/ml of ampicillin and incubated at 37° C. for approximately 3 hours on an Innova 4000 shaker at 250 rpm. 1 ml of a 1M IPTG (isoprpyl-B,D-thiogalactopyranoside) solution was then added to the culture to induce recombinant protein production. The culture was then incubated for a further two hours. The cells were harvested by centrifugation for 10 min at 6000 rpm in 3×500 ml polypropylene bottles using a JA 10 rotor in an Avanti J25 centrifuge. The cell pellet was resuspended in 40 ml of 25% sucrose, 5 mM Tris-hydrochloride, pH 8.0 and frozen at −70° C. for 15 min. The frozen cells were thawed at room temperature and mixed with 10 ml of Lysozyme (Sigma, 10 mg/ml in 250 mM Tris-hydrochloride, pH 8.0). After incubation for 15 min on ice, 300 ml of lysis buffer (2% Triton X100, 50 mM EDTA, 100 mM Tris-hydrochloride, pH 8.0) was added and mixed by shaking. The lysed cell suspension was then sonicated for 4×30 second bursts at full power with a large probe on a Misonix sonicator. The solution was split into 2×250 ml centrifuge bottles and centrifuged for 25 min at 10000 rpm in a JA 14 rotor. The inclusion body pellets were washed by resuspending in 100 ml of double-distilled water and centrifuging to collect the inclusion bodies. This washing procedure was repeated once more and the final inclusion body pellet was suspended in 10 ml of double-distilled water and stored at −20° C. until needed.

All of the isolated fusion proteins were tested by SDS-PAGE to determine their identity by molecular weight, concentration and purity, by comparing the proteins to known standards. 10 μl aliquots of each fusion protein were solubilized with 10 μl of 8M Urea and 2 μl of the solubilized protein was then mixed with 100 μl of 1×SDS-PAGE loading buffer. The loading buffer samples were heated to 94° C. for 5 min and run on a 10% polyacrylamide gel. Recombinant LKT 114 from pCB150 was also run as a control.

EXAMPLE 5

In Vivo Biologic Effect of LKT-Myostatin Peptide Fusion Proteins

To test the ability of the fusion proteins comprising multiple copies of various peptides of myostatin fused to a carrier protein to manifest a biologic effect in vivo, the following vaccination trial was preformed. Recombinant LKT-myostatin peptide fusion proteins were prepared as described above. Vaccines for each were prepared by solubilizing each of the fusion proteins in a final concentration of 6M Urea (used for the first injection) or 4M Guanidine-HCl (used for all subsequent injections). To 2.5 ml (used for the first two injections) or 1.5 ml (used for the last injection) aliquots of VSA-3 adjuvant (a modified Emulsigen Plus adjuvant) 1250 μg of each solubilized protein was added and mixed by 5×5 sec bursts with a Misonix sonicator with a microtip probe at a power setting of 5. To these mixtures, 50 μl of a 1% Thimerosal solution and PBS pH 7.4 (Phosphate Buffer Saline) to a final volume of 5 ml were added and the mixtures sonicated again. A volume of 200 μl was used for each injection. Each injection contained 50 μg of fusion protein. This initial injection (day 0) was given at 3–4 weeks of age with subsequent injections at days 28 and 56.

Figure 18:
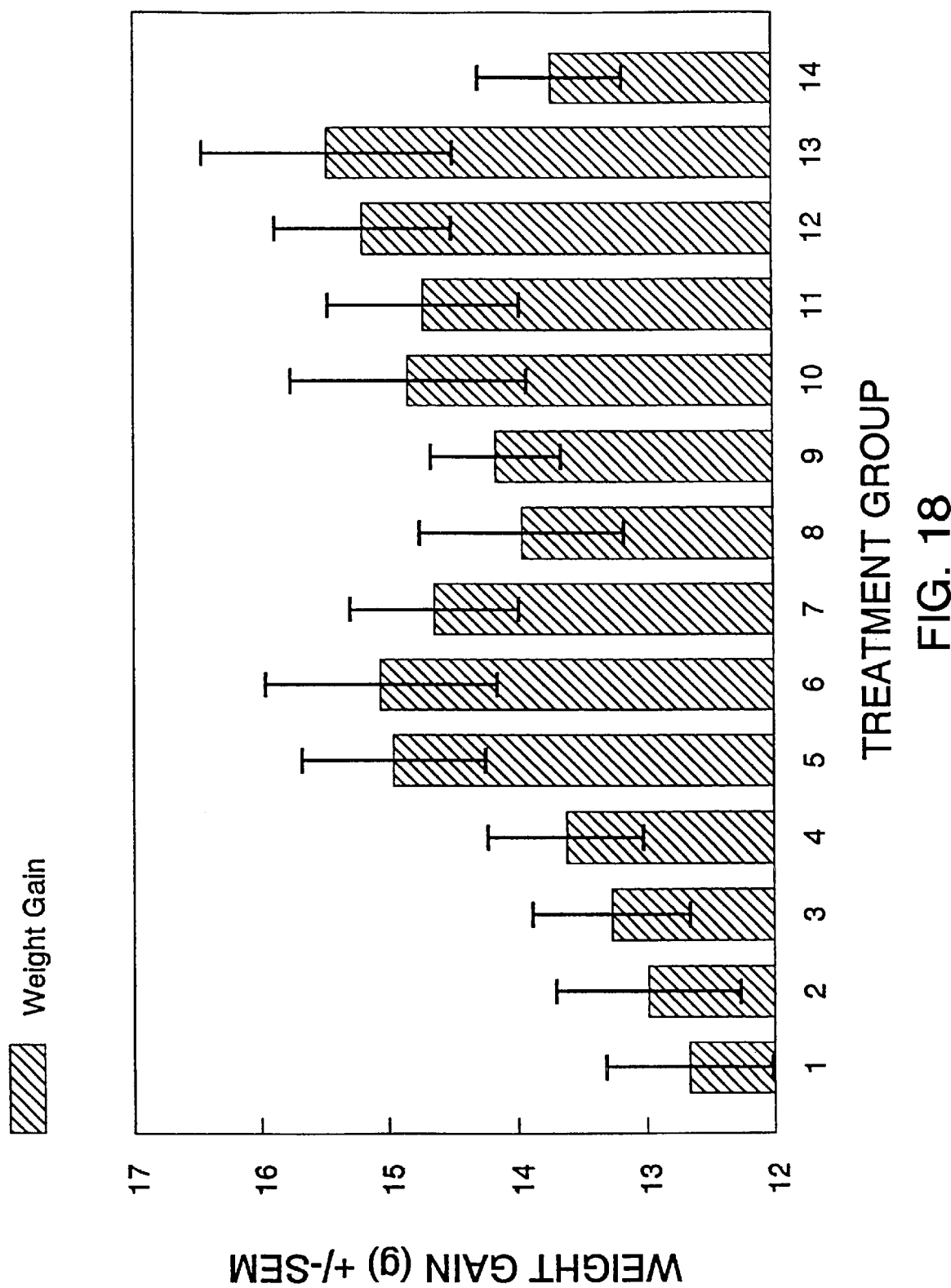
FIG. 18 shows the amount of weight gain in animals treated with myostatin peptide immunogens, as described in the examples.

Fourteen treatment groups each contained 15 CD1 Swiss mice. The treatment groups were as follows (see Table 1): Group 1 no vaccination control, Group 2 adjuvant only control, Group 3 pCB150 carrier protein control, Groups 4 to 13 pJS121 to pJS130 test proteins, Group 14 pCB317 test protein. The mice were weighed weekly to determine weight gain over the course of the 98 day experiment. The results of this trial are summarized in Table 2 and FIG. 18. Guanidine-HCl was used as the solubilizing agent of choice as it appeared to provide improved protein stability over Urea in the vaccine formulation. The concentration of VSA-3 was reduced from 50% to 30% in the vaccine formulation in an effort to reduce injection site reactions.

TABLE 1

| Treatment Group | Myos Oligo | Plasmid |
| --- | --- | --- |
| 1 | — | — |
| 2 | — | — |
| 3 | — | pCB150 |
| 4 | 1 | pJS121 |
| 5 | 3 | pSJ122 |
| 6 | 5 | pSJ123 |
| 7 | 7 | pJS124 |
| 8 | 9 | pJS125 |
| 9 | 11 | pJS126 |
| 10 | 13 | pJS127 |
| 11 | 15 | pJS128 |
| 12 | 17 | pJS129 |
| 13 | 19 | pJS130 |
| 14 | reconstruction | pCB317 |

TABLE 2

| Treatment Group | Mean Group Weight Day 0 ± SEM | Mean Group Weight Day 98 ± SEM | Mean Group Weight Gain Through Day 84 ± SEM |
| --- | --- | --- | --- |
| 1 Control | 16.67 ± 0.32 | 29.33 ± 0.71 | 12.67 ± 0.65 |
| 2 Control | 16.11 ± 0.25 | 29.09 ± 0.79 | 12.99 ± 0.72 |
| 3 Control | 16.05 ± 0.34 | 29.33 ± 0.70 | 13.27 ± 0.61 |
| 4 Test | 16.39 ± 0.37 | 30.02 ± 0.60 | 13.63 ± 0.60 |
| 5 Test | 15.52 ± 0.35 | 30.48 ± 0.84 | 14.96 ± 0.72 |
| 6 Test | 15.78 ± 0.33 | 30.84 ± 0.99 | 15.06 ± 0.90 |
| 7 Test | 15.72 ± 0.27 | 30.36 ± 0.76 | 14.64 ± 0.65 |
| 8 Test | 15.46 ± 0.25 | 29.42 ± 0.84 | 13.96 ± 0.79 |
| 9 Test | 15.32 ± 0.32 | 29.48 ± 0.54 | 14.16 ± 0.50 |
| 10 Test | 16.44 ± 0.31 | 31.27 ± 0.92 | 14.85 ± 0.92 |
| 11 Test | 16.30 ± 0.41 | 31.02 ± 0.70 | 14.72 ± 0.75 |
| 12 Test | 15.54 ± 0.28 | 30.73 ± 0.71 | 15.19 ± 0.69 |
| 13 Test | 15.57 ± 0.30 | 31.04 ± 0.96 | 15.47 ± 0.99 |
| 14 Test | 15.51 ± 0.20 | 29.25 ± 0.62 | 13.73 ± 0.56 |

EXAMPLE 6

Statistical Analysis of Trial Results

Statistical analysis of the trial results was performed using a statistical software package (Statistix Version 1.0). In this trial, all control groups had very similar mean total weights, while several test groups had elevated mean total weights. A one-way ANOVA on the weight gain over the 98 days of the experiment was performed. An LSD comparison of means test indicated that treatment group 13 was significantly different from any of the control groups. Test groups 12 and 6 were significantly different from two of the three control groups. The treatment groups were also analyzed by grouping them into controls (groups 1–3) and test group (groups 4–14). A one-way ANOVA on the weight gains from these two groups was performed. An LSD comparison of means test indicated that the group that received a test treatment was significantly different from the control group.

Deposits of Strains Useful in Practicing the Invention

A deposit of biologically pure cultures of the following strains was made with the American Type Culture Collection (ATCC), 10801 University Boulevard, Manassas, Va. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 U.S.C. §122 and the Commissioner's rules pursuant thereto (including 37 C.F.R. §1.12). Upon the granting of a patent, all restrictions on the availability to the public of the deposited cultures will be irrevocably removed.

These deposits are provided merely as convenience to those of skill in the art, and are not-an admission that a deposit is required under 35 U.S.C. §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| pAA352 in *E. coli* W1485 | March 30, 1990 | 68283 |
| pCB113 in *E. coli* JM105 | February 1, 1995 | 69749 |
| pCB150 in *E. coli* TOP10F' | February 18, 1999 | 207117 |
| pJS123 in *E. coli* TOP10F' | February 10, 1999 | 207093 |
| pJS127 in *E. coli* TOP10F' | February 10, 1999 | 207092 |
| pJS130 in *E. coli* TOP10F' | February 10, 1999 | 207091 |

Thus, immunogenic myostatin peptides, multimers and immunoconjugates are disclosed, as are methods of making and using the same. Although preferred embodiments of the subject invention have been described in some detail, it is understood that obvious variations can be made without departing from the spirit and the scope of the invention as defined by the appended claims.

---

We claim:

1. A myostatin multimer comprising two or more selected myostatin immunogens, wherein each of said myostatin immunogens independently comprises an amino acid sequence selected from the group consisting of amino acids 3–18, inclusive of SEQ ID NO:4; amino acids 3–15, inclusive of SEQ ID NO:6; amino acids 3–17, inclusive, of SEQ ID NO:8; amino acids 3–16, inclusive of SEQ ID NO:10; amino acids 3–22, inclusive of SEQ ID NO:12; amino acids 3–25, inclusive of SEQ ID NO:14; amino acids 3–22, inclusive of SEQ ID NO:16; amino acids 3–19, inclusive, of SEQ ID NO:18; amino acids 3–18, inclusive of SEQ ID NO:20; and amino acids 3–18, inclusive, of SEQ ID NO:22.

2. A myostatin multimer comprising two or more selected myostatin immunogens, wherein at least one of said selected myostatin immunogens comprises the amino acid sequence Lys-Arg-Ser-Arg-Arg-Asp (SEQ ID NO:37).

3. A myostatin multimer comprising two or more selected myostatin immunogens, wherein at least one of said selected myostatin immunogens comprises the amino acid sequence Lys-Glu-Asn-Val-Glu-Lys-Glu (SEQ ID NO:38).

4. A myostatin multimer comprising two or more selected myostatin immunogens, wherein at least one of said selected myostatin immunogens comprises the amino acid sequence Ser-Leu-Lys-Asp-Asp-Asp (SEQ ID NO:39).

5. The myostatin multimer of claim 1, wherein said myostatin immunogens are myostatin peptides and said multimer comprises a molecule according to the general formula (MP-X-MP)y, wherein MP is a myostatin peptide, X is selected from the group consisting of a peptide linkage, an amino acid spacer group, a leukotoxin polypeptide and [MP]$_n$, where n is greater than or equal to 1, and y is greater than or equal to 1.

6. The myostatin multimer of claim 5, wherein X comprises an amino acid spacer group including at least one helper T-cell epitope.

7. The myostatin multimer of claim 5, wherein the myostatin peptides present in the multimer comprise the same amino acid sequence.

8. The myostatin multimer of claim 5, wherein the myostatin peptides present in the multimer comprise different amino acid sequences.

9. The myostatin multimer of claim 1, wherein said multimer comprises at least two copies of SEQ ID NO:4.

10. The myostatin multimer of claim 9, wherein said multimer comprises six copies of SEQ ID NO:4 fused to LKT 114 as depicted in FIGS. 15A–15D (SEQ ID NO:26).

11. The myostatin multimer of claim 1, wherein said multimer comprises at least two copies of SEQ ID NO:6.

12. The myostatin multimer of claim 11, wherein said multimer comprises eight copies of SEQ ID NO:6 fused to LKT 114 as depicted in FIGS. 15A–15D (SEQ ID NO:26).

13. The myostatin multimer of claim 1, wherein said multimer comprises at least two copies of SEQ ID NO:8.

14. The myostatin multimer of claim 13, wherein said multimer comprises eight copies of SEQ ID NO:8 fused to LKT 114 as depicted in FIGS. 15A–15D (SEQ ID NO:26).

15. The myostatin multimer of claim 1, wherein said multimer comprises at least two copies of SEQ ID NO:10.

16. The myostatin multimer of claim 15, wherein said multimer comprises eight copies of SEQ ID NO:10 fused to LKT 114 as depicted in FIGS. 15A–15D (SEQ ID NO:26).

17. The myostatin multimer of claim 1, wherein said multimer comprises at least two copies of SEQ ID NO:12.

18. The myostatin multimer of claim 17, wherein said multimer comprises six copies of SEQ ID NO:12 fused to LKT 114 as depicted in FIGS. 15A–15D (SEQ ID NO:26).

19. The myostatin multimer of claim 1, wherein said multimer comprises at least two copies of SEQ ID NO:14.

20. The myostatin multimer of claim 19, wherein said multimer comprises four copies of SEQ ID NO:14 fused to LKT 114 as depicted in FIGS. 15A–15D (SEQ ID NO:26).

21. The myostatin multimer of claim 1, wherein said multimer comprises at least two copies of SEQ ID NO:16.

22. The myostatin multimer of claim 21, wherein said multimer comprises six copies of SEQ ID NO:16 fused to LKT 114 as depicted in FIGS. 15A–15D (SEQ ID NO:26).

23. The myostatin multimer of claim 1, wherein said multimer comprises at least two copies of SEQ ID NO:18.

24. The myostatin multimer of claim 23, wherein said multimer comprises four copies of SEQ ID NO:18 fused to LKT 114 as depicted in FIGS. 15A–15D (SEQ ID NO:26).

25. The myostatin multimer of claim 1, wherein said multimer comprises at least two copies of SEQ ID NO:20.

26. The myostatin multimer of claim 25, wherein said multimer comprises eight copies of SEQ ID NO:20 fused to LKT 114 as depicted in FIGS. 15A–15D (SEQ ID NO:26).

27. The myostatin multimer of claim 1, wherein said multimer comprises at least two copies of SEQ ID NO:22.

28. The myostatin multimer of claim 27, wherein said multimer comprises four copies of SEQ ID NO:22 fused to LKT 114 as depicted in FIGS. 15A–15D (SEQ ID NO:26).

\* \* \* \* \*

SEQUENCE LISTING

```
<160> NUMBER OF SEQ ID NOS: 39

<210> SEQ ID NO 1
<211> LENGTH: 1128
<212> TYPE: DNA
<213> ORGANISM: bos taurus

<400> SEQUENCE: 1
atgcaaaaac tgcaaatctc tgtttatatt tacctattta cgctgattgt tgctggccca        60
gtggatctga atgagaacag cgagcagaag gaaaatgtgg aaaagagggg gctgtgtaat       120
gcatgtttgt ggagggaaaa cactacatcc tcaagactag aagccataaa aatccaaatc       180
ctcagtaaac ttcgcctgga aacagctcct aacatcagca aagatgctat cagacaactt       240
ttgcccaagg ctcctccact cctggaactg attgatcagt tcgatgtcca gagagatgcc       300
agcagtgacg gctccttgga agacgatgac taccacgcca ggacggaaac ggtcattacc       360
atgcccacgg agtctgatct tctaacgcaa gtggaaggaa aacccaaatg ttgcttcttt       420
aaatttagct ctaagataca atacaataaa ctagtaaagg cccaactgtg gatatatctg       480
aggcctgtca agactcctgc gacagtgttt gtgcaaatcc tgagactcat caaacccatg       540
aaagacggta caaggtatac tggaatccga tctctgaaac ttgacatgaa cccaggcact       600
ggtatttggc agagcattga tgtgaagaca gtgttgcaga actggctcaa acaacctgaa       660
tccaacttag gcattgaaat caaagcttta gatgagaatg gccatgatct tgctgtaacc       720
ttcccagaac aggagaaga tggactgact ccttttttag aagtcaaggt aacagacaca       780
ccaaaaagat ctaggagaga ttttgggctt gattgtgatg aacactccac agaatctcga       840
tgctgtcgct acccctcac ggtggatttt gaagcttttg gatgggattg gattattgca       900
cctaaaagat ataaggccaa ttactgctct ggagaatgtg aatttgtatt tttgcaaaag       960
tatcctcata cccatcttgt gcaccaagca aaccccagag gttcagccgg ccctgctgt       1020
```

-continued

```
actcctacaa agatgtctcc aattaatatg ctatatttta atggcgaagg acaaataata    1080
tacgggaaga ttccagccat ggtagtagat cgctgtgggt gctcatga                1128
```

<210> SEQ ID NO 2
<211> LENGTH: 375
<212> TYPE: PRT
<213> ORGANISM: bos taurus

<400> SEQUENCE: 2

```
Met Gln Lys Leu Gln Ile Ser Val Tyr Ile Tyr Leu Phe Thr Leu Ile
  1               5                  10                  15

Val Ala Gly Pro Val Asp Leu Asn Glu Asn Ser Glu Gln Lys Glu Asn
                 20                  25                  30

Val Glu Lys Glu Gly Leu Cys Asn Ala Cys Leu Trp Arg Glu Asn Thr
             35                  40                  45

Thr Ser Ser Arg Leu Glu Ala Ile Lys Ile Gln Ile Leu Ser Lys Leu
         50                  55                  60

Arg Leu Glu Thr Ala Pro Asn Ile Ser Lys Asp Ala Ile Arg Gln Leu
 65                  70                  75                  80

Leu Pro Lys Ala Pro Pro Leu Glu Leu Ile Asp Gln Phe Asp Val
                 85                  90                  95

Gln Arg Asp Ala Ser Ser Asp Gly Ser Leu Glu Asp Asp Tyr His
                100                 105                 110

Ala Arg Thr Glu Thr Val Ile Thr Met Pro Thr Glu Ser Asp Leu Leu
            115                 120                 125

Thr Gln Val Glu Gly Lys Pro Lys Cys Cys Phe Phe Lys Phe Ser Ser
        130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350
```

Phe Asn Gly Glu Gly Gln Ile Ile Tyr Gly Lys Ile Pro Ala Met Val
            355                 360                 365

Val Asp Arg Cys Gly Cys Ser
    370                 375

<210> SEQ ID NO 3
<211> LENGTH: 60
<212> TYPE: DNA
<213> ORGANISM: Artificial Sequence
<220> FEATURE:
<221> NAME/KEY: CDS
<222> LOCATION: (1)..(60)
<223> OTHER INFORMATION: Description of Artificial Sequence: MYOS 1
      peptide coding sequence, Figure 2

<400> SEQUENCE: 3 gga tcc cgt tct cgt cgc gac ttt ggt ctg gac tgc gac gaa cat tct        48
Gly Ser Arg Ser Arg Arg Asp Phe Gly Leu Asp Cys Asp Glu His Ser
  1               5                  10                  15 acc gaa aga tct                                                        60
Thr Glu Arg Ser
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: MYOS 1
      peptide coding sequence, Figure 2

<400> SEQUENCE: 4

Gly Ser Arg Ser Arg Arg Asp Phe Gly Leu Asp Cys Asp Glu His Ser
  1               5                  10                  15

Thr Glu Arg Ser
            20

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: MYOS 3
      peptide coding sequence, Figure 3
<221> NAME/KEY: CDS
<222> LOCATION: (1)..(51)

<400> SEQUENCE: 5 gga tcc tct cgt tgc tgt cgc tat ccg ctg acc gtt gac ttc gaa aga        48
Gly Ser Ser Arg Cys Cys Arg Tyr Pro Leu Thr Val Asp Phe Glu Arg
  1               5                  10                  15 tct                                                                    51
Ser

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: MYOS 3
      peptide coding sequence, Figure 3

<400> SEQUENCE: 6

Gly Ser Ser Arg Cys Cys Arg Tyr Pro Leu Thr Val Asp Phe Glu Arg
  1               5                  10                  15

Ser

-continued

```
<210> SEQ ID NO 7
<211> LENGTH: 57
<212> TYPE: DNA
<213> ORGANISM: Artificial Sequence
<220> FEATURE:
<223> OTHER INFORMATION: Description of Artifical Sequence: MYOS 5
      peptide coding sequence, Figure 4
<221> NAME/KEY: CDS
<222> LOCATION: (1)..(57)

<400> SEQUENCE: 7 gga tcc ttc gaa gct ttt ggt tgg gac tgg atc att gca ccg aaa cgt     48
Gly Ser Phe Glu Ala Phe Gly Trp Asp Trp Ile Ile Ala Pro Lys Arg
 1               5                  10                  15 tat aga tct                                                         57
Tyr Arg Ser <210> SEQ ID NO 8
<211> LENGTH: 19
<212> TYPE: PRT
<213> ORGANISM: Artificial Sequence
<220> FEATURE:
<223> OTHER INFORMATION: Description of Artifical Sequence: MYOS 5
      peptide coding sequence, Figure 4

<400> SEQUENCE: 8

Gly Ser Phe Glu Ala Phe Gly Trp Asp Trp Ile Ile Ala Pro Lys Arg
 1               5                  10                  15

Tyr Arg Ser

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: MYOS 7
      peptide coding sequence, Figure 5
<221> NAME/KEY: CDS
<222> LOCATION: (1)..(54)

<400> SEQUENCE: 9 gga tcc aaa cgt tat aaa gct aac tat tgc tct ggt gaa tgc gaa ttc     48
Gly Ser Lys Arg Tyr Lys Ala Asn Tyr Cys Ser Gly Glu Cys Glu Phe
 1               5                  10                  15 aga tct                                                             54
Arg Ser

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: MYOS 7
      peptide coding sequence, Figure 5

<400> SEQUENCE: 10

Gly Ser Lys Arg Tyr Lys Ala Asn Tyr Cys Ser Gly Glu Cys Glu Phe
 1               5                  10                  15

Arg Ser

<210> SEQ ID NO 11
<211> LENGTH: 72
<212> TYPE: DNA
<213> ORGANISM: Artificial Sequence
<220> FEATURE:
<223> OTHER INFORMATION: Description of Artificial Sequence: MYOS 9
      peptide coding sequence, Figure 6
```

```
<221> NAME/KEY: CDS
<222> LOCATION: (1)..(72)

<400> SEQUENCE: 11 gga tcc gaa ttc gtt ttc ctg cag aaa tat ccg cat acc cat ctg gtt    48
Gly Ser Glu Phe Val Phe Leu Gln Lys Tyr Pro His Thr His Leu Val
 1               5                  10                  15 cat cag gct aac ccg cgt aga tct                                    72
His Gln Ala Asn Pro Arg Arg Ser
            20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: MYOS 9
      peptide coding sequence, Figure 6

<400> SEQUENCE: 12

Gly Ser Glu Phe Val Phe Leu Gln Lys Tyr Pro His Thr His Leu Val
 1               5                  10                  15

His Gln Ala Asn Pro Arg Arg Ser
            20

<210> SEQ ID NO 13
<211> LENGTH: 81
<212> TYPE: DNA
<213> ORGANISM: Artificial Sequence
<220> FEATURE:
<223> OTHER INFORMATION: Description of Artificial Sequence: MYOS 11
      peptide coding sequence, Figure 7
<221> NAME/KEY: CDS
<222> LOCATION: (1)..(81)

<400> SEQUENCE: 13 gga tcc gct ggt ccg tgc tgt tat ccg acc aaa atg tct ccg atc aac    48
Gly Ser Ala Gly Pro Cys Cys Tyr Pro Thr Lys Met Ser Pro Ile Asn
 1               5                  10                  15 atg ctg tat ttc aac ggt gaa tgc cag aga tct                        81
Met Leu Tyr Phe Asn Gly Glu Cys Gln Arg Ser
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: MYOS 11
      peptide coding sequence, Figure 7

<400> SEQUENCE: 14

Gly Ser Ala Gly Pro Cys Cys Tyr Pro Thr Lys Met Ser Pro Ile Asn
 1               5                  10                  15

Met Leu Tyr Phe Asn Gly Glu Cys Gln Arg Ser
            20                  25

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence: MYOS 13
      peptide coding sequence, Figure 8
<221> NAME/KEY: CDS
<222> LOCATION: (1)..(72)
```

```
<400> SEQUENCE: 15 gga tcc gaa tgc cag atc att tat tgc aaa atc ccg gct atg gtt gta      48
Gly Ser Glu Cys Gln Ile Ile Tyr Cys Lys Ile Pro Ala Met Val Val
  1               5                  10                  15 gac cgt tgc ggt tgt tct aga tct                                      72
Asp Arg Cys Gly Cys Ser Arg Ser
                 20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: MYOS 13
      peptide coding sequence, Figure 8

<400> SEQUENCE: 16

Gly Ser Glu Cys Gln Ile Ile Tyr Cys Lys Ile Pro Ala Met Val Val
  1               5                  10                  15

Asp Arg Cys Gly Cys Ser Arg Ser
                 20

<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: MYOS 15
      peptide coding sequence, Figure 9
<221> NAME/KEY: CDS
<222> LOCATION: (1)..(63)

<400> SEQUENCE: 17 gga tcc gaa cag aaa gaa aac gtt gaa aaa gaa ggt ctg tgc aac gct      48
Gly Ser Glu Gln Lys Glu Asn Val Glu Lys Glu Gly Leu Cys Asn Ala
  1               5                  10                  15 tgc ctg tgg aga tct                                                  63
Cys Leu Trp Arg Ser
                 20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: MYOS 15
      peptide coding sequence, Figure 9

<400> SEQUENCE: 18

Gly Ser Glu Gln Lys Glu Asn Val Glu Lys Glu Gly Leu Cys Asn Ala
  1               5                  10                  15

Cys Leu Trp Arg Ser
                 20

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: MYOS 17
      peptide coding sequence, Figure 10
<221> NAME/KEY: CDS
<222> LOCATION: (1)..(60)
```

```
<400> SEQUENCE: 19 gga tcc cat gac ctg gct gtt acc ttc ccg gaa ccg ggt gaa gac ggt    48
Gly Ser His Asp Leu Ala Val Thr Phe Pro Glu Pro Gly Glu Asp Gly
  1               5                  10                  15 ctg acc aga tct                                                    60
Leu Thr Arg Ser
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: MYOS 17
      peptide coding sequence, Figure 10

<400> SEQUENCE: 20

Gly Ser His Asp Leu Ala Val Thr Phe Pro Glu Pro Gly Glu Asp Gly
  1               5                  10                  15

Leu Thr Arg Ser
            20

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: MYOS 19
      peptide coding sequence, Figure 11
<221> NAME/KEY: CDS
<222> LOCATION: (1)..(60)

<400> SEQUENCE: 21 gga tcc acc ccg ttc ctg gaa gtt aaa gtt acc gac act ccg aaa cgt    48
Gly Ser Thr Pro Phe Leu Glu Val Lys Val Thr Asp Thr Pro Lys Arg
  1               5                  10                  15 tct cgt aga tct                                                    60
Ser Arg Arg Ser
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: MYOS 19
      peptide coding sequence, Figure 11

<400> SEQUENCE: 22

Gly Ser Thr Pro Phe Leu Glu Val Lys Val Thr Asp Thr Pro Lys Arg
  1               5                  10                  15

Ser Arg Arg Ser
            20

<210> SEQ ID NO 23
<211> LENGTH: 372
<212> TYPE: DNA
<213> ORGANISM: Artificial Sequence
<220> FEATURE:
<223> OTHER INFORMATION: Description of Artificial Sequence:
      reconstructed myostatin active region, Figure 13
<221> NAME/KEY: CDS
<222> LOCATION: (1)..(372)
```

-continued

```
<400> SEQUENCE: 23 gga tcc cgt tct cgt cgc gac ttt ggt ctg gac tgc gac gaa cat tct    48
Gly Ser Arg Ser Arg Arg Asp Phe Gly Leu Asp Cys Asp Glu His Ser
  1               5                  10                  15 acc gaa aga tcc tct cgt tgc tgt cgc tat ccg ctg acc gtt gac ttc    96
Thr Glu Arg Ser Ser Arg Cys Cys Arg Tyr Pro Leu Thr Val Asp Phe
             20                  25                  30 gaa gct ttt ggt tgg gac tgg atc att gca ccg aaa cgt tat aga tcc   144
Glu Ala Phe Gly Trp Asp Trp Ile Ile Ala Pro Lys Arg Tyr Arg Ser
         35                  40                  45 aaa cgt tat aaa gct aac tat tgc tct ggt gaa tgc gaa ttc gtt ttc   192
Lys Arg Tyr Lys Ala Asn Tyr Cys Ser Gly Glu Cys Glu Phe Val Phe
 50                  55                  60 ctg cag aaa tat ccg cat acc cat ctg gtt cat cag gct aac ccg cgt   240
Leu Gln Lys Tyr Pro His Thr His Leu Val His Gln Ala Asn Pro Arg
 65                  70                  75                  80 aga tcc gct ggt ccg tgc tgt tat ccg acc aaa atg tct ccg atc aac   288
Arg Ser Ala Gly Pro Cys Cys Tyr Pro Thr Lys Met Ser Pro Ile Asn
                 85                  90                  95 atg ctg tat ttc aac ggt gaa tgc cag atc att tat tgc aaa atc ccg   336
Met Leu Tyr Phe Asn Gly Glu Cys Gln Ile Ile Tyr Cys Lys Ile Pro
            100                 105                 110 gct atg gtt gta gac cgt tgc ggt tgt tct aga tct                   372
Ala Met Val Val Asp Arg Cys Gly Cys Ser Arg Ser
            115                 120

<210> SEQ ID NO 24
<211> LENGTH: 124
<212> TYPE: PRT
<213> ORGANISM: Artificial Sequence
<220> FEATURE:
<223> OTHER INFORMATION: Description of Artificial Sequence:
      reconstructed myostatin active region, Figure 13

<400> SEQUENCE: 24

Gly Ser Arg Ser Arg Arg Asp Phe Gly Leu Asp Cys Asp Glu His Ser
  1               5                  10                  15

Thr Glu Arg Ser Ser Arg Cys Cys Arg Tyr Pro Leu Thr Val Asp Phe
             20                  25                  30

Glu Ala Phe Gly Trp Asp Trp Ile Ile Ala Pro Lys Arg Tyr Arg Ser
         35                  40                  45

Lys Arg Tyr Lys Ala Asn Tyr Cys Ser Gly Glu Cys Glu Phe Val Phe
 50                  55                  60

Leu Gln Lys Tyr Pro His Thr His Leu Val His Gln Ala Asn Pro Arg
 65                  70                  75                  80

Arg Ser Ala Gly Pro Cys Cys Tyr Pro Thr Lys Met Ser Pro Ile Asn
                 85                  90                  95

Met Leu Tyr Phe Asn Gly Glu Cys Gln Ile Ile Tyr Cys Lys Ile Pro
            100                 105                 110

Ala Met Val Val Asp Arg Cys Gly Cys Ser Arg Ser
            115                 120

<210> SEQ ID NO 25
<211> LENGTH: 1473
<212> TYPE: DNA
<213> ORGANISM: Artificial Sequence
<220> FEATURE:
<223> OTHER INFORMATION: Description of Artificial Sequence: leukotoxin
      polypeptide carrier, Figures 15A-15D
<221> NAME/KEY: CDS
<222> LOCATION: (1)..(1473)
```

-continued

```
<400> SEQUENCE: 25 atg gct act gtt ata gat cta agc ttc cca aaa act ggg gca aaa aaa        48
Met Ala Thr Val Ile Asp Leu Ser Phe Pro Lys Thr Gly Ala Lys Lys
 1               5                  10                  15 att atc ctc tat att ccc caa aat tac caa tat gat act gaa caa ggt        96
Ile Ile Leu Tyr Ile Pro Gln Asn Tyr Gln Tyr Asp Thr Glu Gln Gly
             20                  25                  30 aat ggt tta cag gat tta gtc aaa gcg gcc gaa gag ttg ggg att gag       144
Asn Gly Leu Gln Asp Leu Val Lys Ala Ala Glu Glu Leu Gly Ile Glu
         35                  40                  45 gta caa aga gaa gaa cgc aat aat att gca aca gct caa acc agt tta       192
Val Gln Arg Glu Glu Arg Asn Asn Ile Ala Thr Ala Gln Thr Ser Leu
 50                  55                  60 ggc acg att caa acc gct att ggc tta act gag cgt ggc att gtg tta       240
Gly Thr Ile Gln Thr Ala Ile Gly Leu Thr Glu Arg Gly Ile Val Leu
 65                  70                  75                  80 tcc gct cca caa att gat aaa ttg cta cag aaa act aaa gca ggc caa       288
Ser Ala Pro Gln Ile Asp Lys Leu Leu Gln Lys Thr Lys Ala Gly Gln
                 85                  90                  95 gca tta ggt tct gcc gaa agc att gta caa aat gca aat aaa gcc aaa       336
Ala Leu Gly Ser Ala Glu Ser Ile Val Gln Asn Ala Asn Lys Ala Lys
            100                 105                 110 act gta tta tct ggc att caa tct att tta ggc tca gta ttg gct gga       384
Thr Val Leu Ser Gly Ile Gln Ser Ile Leu Gly Ser Val Leu Ala Gly
        115                 120                 125 atg gat tta gat gag gcc tta cag aat aac agc aac caa cat gct ctt       432
Met Asp Leu Asp Glu Ala Leu Gln Asn Asn Ser Asn Gln His Ala Leu
    130                 135                 140 gct aaa gct ggc ttg gag cta aca aat tca tta att gaa aat att gct       480
Ala Lys Ala Gly Leu Glu Leu Thr Asn Ser Leu Ile Glu Asn Ile Ala
145                 150                 155                 160 aat tca gta aaa aca ctt gac gaa ttt ggt gag caa att agt caa ttt       528
Asn Ser Val Lys Thr Leu Asp Glu Phe Gly Glu Gln Ile Ser Gln Phe
                165                 170                 175 ggt tca aaa cta caa aat atc aaa ggc tta ggg act tta gga gac aaa       576
Gly Ser Lys Leu Gln Asn Ile Lys Gly Leu Gly Thr Leu Gly Asp Lys
            180                 185                 190 ctc aaa aat atc ggt gga ctt gat aaa gct ggc ctt ggt tta gat gtt       624
Leu Lys Asn Ile Gly Gly Leu Asp Lys Ala Gly Leu Gly Leu Asp Val
        195                 200                 205 atc tca ggg cta tta tcg ggc gca acc gct gca ctt gta ctt gca gat       672
Ile Ser Gly Leu Leu Ser Gly Ala Thr Ala Ala Leu Val Leu Ala Asp
    210                 215                 220 aaa aat gct tca aca gct aaa aaa gtg ggt gcg ggt ttt gaa ttg gca       720
Lys Asn Ala Ser Thr Ala Lys Lys Val Gly Ala Gly Phe Glu Leu Ala
225                 230                 235                 240 aac caa gtt gtt ggt aat att acc aaa gcc gtt tct tct tac att tta       768
Asn Gln Val Val Gly Asn Ile Thr Lys Ala Val Ser Ser Tyr Ile Leu
                245                 250                 255 gcc caa cgt gtt gca gca ggt tta tct tca act ggg cct gtg gct gct       816
Ala Gln Arg Val Ala Ala Gly Leu Ser Ser Thr Gly Pro Val Ala Ala
            260                 265                 270 tta att gct tct act gtt tct ctt gcg att agc cca tta gca ttt gcc       864
Leu Ile Ala Ser Thr Val Ser Leu Ala Ile Ser Pro Leu Ala Phe Ala
        275                 280                 285 ggt att gcc gat aaa ttt aat cat gca aaa agt tta gag agt tat gcc       912
Gly Ile Ala Asp Lys Phe Asn His Ala Lys Ser Leu Glu Ser Tyr Ala
    290                 295                 300
```

-continued

```
gaa cgc ttt aaa aaa tta ggc tat gac gga gat aat tta tta gca gaa      960
Glu Arg Phe Lys Lys Leu Gly Tyr Asp Gly Asp Asn Leu Leu Ala Glu
305                 310                 315                 320 tat cag cgg gga aca ggg act att gat gca tcg gtt act gca att aat     1008
Tyr Gln Arg Gly Thr Gly Thr Ile Asp Ala Ser Val Thr Ala Ile Asn
                325                 330                 335 acc gca ttg gcc gct att gct ggt ggt gtg tct gct gct gca gcc gat     1056
Thr Ala Leu Ala Ala Ile Ala Gly Gly Val Ser Ala Ala Ala Ala Asp
            340                 345                 350 tta aca ttt gaa aaa gtt aaa cat aat ctt gtc atc acg aat agc aaa     1104
Leu Thr Phe Glu Lys Val Lys His Asn Leu Val Ile Thr Asn Ser Lys
        355                 360                 365 aaa gag aaa gtg acc att caa aac tgg ttc cga gag gct gat ttt gct     1152
Lys Glu Lys Val Thr Ile Gln Asn Trp Phe Arg Glu Ala Asp Phe Ala
    370                 375                 380 aaa gaa gtg cct aat tat aaa gca act aaa gat gag aaa atc gaa gaa     1200
Lys Glu Val Pro Asn Tyr Lys Ala Thr Lys Asp Glu Lys Ile Glu Glu
385                 390                 395                 400 atc atc ggt caa aat ggc gag cgg atc acc tca aag caa gtt gat gat     1248
Ile Ile Gly Gln Asn Gly Glu Arg Ile Thr Ser Lys Gln Val Asp Asp
                405                 410                 415 ctt atc gca aaa ggt aac ggc aaa att acc caa gat gag cta tca aaa     1296
Leu Ile Ala Lys Gly Asn Gly Lys Ile Thr Gln Asp Glu Leu Ser Lys
            420                 425                 430 gtt gtt gat aac tat gaa ttg ctc aaa cat agc aaa aat gtg aca aac     1344
Val Val Asp Asn Tyr Glu Leu Leu Lys His Ser Lys Asn Val Thr Asn
        435                 440                 445 agc tta gat aag tta atc tca tct gta agt gca ttt acc tcg tct aat     1392
Ser Leu Asp Lys Leu Ile Ser Ser Val Ser Ala Phe Thr Ser Ser Asn
    450                 455                 460 gat tcg aga aat gta tta gtg gct cca act tca atg ttg gat caa agt     1440
Asp Ser Arg Asn Val Leu Val Ala Pro Thr Ser Met Leu Asp Gln Ser
465                 470                 475                 480 tta tct tct ctt caa ttt gct agg gga tcc tag                         1473
Leu Ser Ser Leu Gln Phe Ala Arg Gly Ser
                485                 490

<210> SEQ ID NO 26
<211> LENGTH: 490
<212> TYPE: PRT
<213> ORGANISM: Artificial Sequence
<220> FEATURE:
<223> OTHER INFORMATION: Description of Artificial Sequence: leukotoxin
      polypeptide carrier, Figures 15A-15D

<400> SEQUENCE: 26

Met Ala Thr Val Ile Asp Leu Ser Phe Pro Lys Thr Gly Ala Lys Lys
  1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
 65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110
```

```
Thr Val Leu Ser Gly Ile Gln Ser Ile Leu Gly Ser Val Leu Ala Gly
            115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
                180                 185                 190

Leu Lys Asn Ile Gly Gly Leu Asp Lys Ala Gly Leu Gly Leu Asp Val
                195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
                260                 265                 270

Leu Ile Ala Ser Thr Val Ser Leu Ala Ile Ser Pro Leu Ala Phe Ala
    275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Asp
                340                 345                 350

Leu Thr Phe Glu Lys Val Lys His Asn Leu Val Ile Thr Asn Ser Lys
                355                 360                 365

Lys Glu Lys Val Thr Ile Gln Asn Trp Phe Arg Glu Ala Asp Phe Ala
    370                 375                 380

Lys Glu Val Pro Asn Tyr Lys Ala Thr Lys Asp Glu Lys Ile Glu Glu
385                 390                 395                 400

Ile Ile Gly Gln Asn Gly Glu Arg Ile Thr Ser Lys Gln Val Asp Asp
                405                 410                 415

Leu Ile Ala Lys Gly Asn Gly Lys Ile Thr Gln Asp Glu Leu Ser Lys
                420                 425                 430

Val Val Asp Asn Tyr Glu Leu Leu Lys His Ser Lys Asn Val Thr Asn
                435                 440                 445

Ser Leu Asp Lys Leu Ile Ser Ser Val Ser Ala Phe Thr Ser Ser Asn
    450                 455                 460

Asp Ser Arg Asn Val Leu Val Ala Pro Thr Ser Met Leu Asp Gln Ser
465                 470                 475                 480

Leu Ser Ser Leu Gln Phe Ala Arg Gly Ser
                485                 490

<210> SEQ ID NO 27
<211> LENGTH: 376
<212> TYPE: PRT
<213> ORGANISM: Mus musculus
```

-continued

```
<400> SEQUENCE: 27

Met Met Gln Lys Leu Gln Met Tyr Val Tyr Ile Tyr Leu Phe Met Leu
 1               5                  10                  15

Ile Ala Ala Gly Pro Val Asp Leu Asn Glu Gly Ser Glu Arg Glu Glu
             20                  25                  30

Asn Val Glu Lys Glu Gly Leu Cys Asn Ala Cys Ala Trp Arg Gln Asn
         35                  40                  45

Thr Arg Tyr Ser Arg Ile Glu Ala Ile Lys Ile Gln Ile Leu Ser Lys
     50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375

<210> SEQ ID NO 28
<211> LENGTH: 376
<212> TYPE: PRT
<213> ORGANISM: Rattus norvegicus
```

```
<400> SEQUENCE: 28

Met Ile Gln Lys Pro Gln Met Tyr Val Tyr Ile Tyr Leu Phe Val Leu
  1               5                  10                  15

Ile Ala Ala Gly Pro Val Asp Leu Asn Glu Asp Ser Glu Arg Glu Ala
             20                  25                  30

Asn Val Glu Lys Glu Gly Leu Cys Asn Ala Cys Ala Trp Arg Gln Asn
         35                  40                  45

Thr Arg Tyr Ser Arg Ile Glu Ala Ile Lys Ile Gln Ile Leu Ser Lys
     50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
370                 375

<210> SEQ ID NO 29
<211> LENGTH: 375
<212> TYPE: PRT
<213> ORGANISM: Homo sapiens
```

```
<400> SEQUENCE: 29

Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
     50                  55                  60

Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
370                 375

<210> SEQ ID NO 30
<211> LENGTH: 375
<212> TYPE: PRT
<213> ORGANISM: Papio hamadryas
```

```
<400> SEQUENCE: 30

Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Leu Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
370                 375

<210> SEQ ID NO 31
<211> LENGTH: 375
<212> TYPE: PRT
<213> ORGANISM: bos taurus
```

```
<400> SEQUENCE: 31

Met Gln Lys Leu Gln Ile Ser Val Tyr Ile Tyr Leu Phe Met Leu Ile
 1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Leu Trp Arg Glu Asn Thr
         35                  40                  45

Thr Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Arg Ala Pro Pro Leu Leu Glu Leu Ile Asp Gln Phe Asp Val
                 85                  90                  95

Gln Arg Asp Ala Ser Ser Asp Gly Ser Leu Glu Asp Asp Tyr His
             100                 105                 110

Ala Arg Thr Glu Thr Val Ile Thr Met Pro Thr Glu Ser Asp Leu Leu
         115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Glu Gly Gln Ile Ile Tyr Gly Lys Ile Pro Ala Met Val
        355                 360                 365

Val Asp Arg Cys Gly Cys Ser
    370                 375

<210> SEQ ID NO 32
<211> LENGTH: 375
<212> TYPE: PRT
<213> ORGANISM: Sus scrofa
```

```
<400> SEQUENCE: 32

Met Gln Lys Leu Gln Ile Tyr Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Met Trp Arg Gln Asn Thr
        35                  40                  45

Lys Ser Ser Arg Leu Glu Ala Ile Lys Ile Gln Ile Leu Ser Lys Leu
    50                  55                  60

Arg Leu Glu Thr Ala Pro Asn Ile Ser Lys Asp Ala Ile Arg Gln Leu
65                  70                  75                  80

Leu Pro Arg Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Leu Leu
            115                 120                 125

Met Gln Val Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 33
<211> LENGTH: 375
<212> TYPE: PRT
<213> ORGANISM: Ovis aries
```

```
<400> SEQUENCE: 33

Met Gln Lys Leu Gln Ile Phe Val Tyr Ile Tyr Leu Phe Met Leu Leu
 1               5                  10                  15

Val Ala Gly Pro Val Asp Leu Asn Glu Asn Ser Glu Gln Lys Glu Asn
             20                  25                  30

Val Glu Lys Lys Gly Leu Cys Asn Ala Cys Leu Trp Arg Gln Asn Asn
         35                  40                  45

Lys Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Arg Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Tyr His
            100                 105                 110

Val Thr Thr Glu Thr Val Ile Thr Met Pro Thr Glu Ser Asp Leu Leu
            115                 120                 125

Ala Glu Val Gln Glu Lys Pro Lys Cys Cys Phe Phe Lys Phe Ser Ser
130                 135                 140

Lys Ile Gln His Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Glu Pro Gly Glu Glu Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Leu Phe Leu Gln Lys
305                 310                 315                 320

Tyr Pro His Thr His Leu Val His Gln Ala Asn Pro Lys Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Gly Met Val
            355                 360                 365

Val Asp Arg Cys Gly Cys Ser
370                 375

<210> SEQ ID NO 34
<211> LENGTH: 375
<212> TYPE: PRT
<213> ORGANISM: Gallus gallus
```

```
<400> SEQUENCE: 34

Met Gln Lys Leu Ala Val Tyr Val Tyr Ile Tyr Leu Phe Met Gln Ile
  1               5                  10                  15

Ala Val Asp Pro Val Ala Leu Asp Gly Ser Ser Gln Pro Thr Glu Asn
             20                  25                  30

Ala Glu Lys Asp Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
 50                  55                  60

Arg Leu Glu Gln Ala Pro Asn Ile Ser Arg Asp Val Ile Lys Gln Leu
 65                  70                  75                  80

Leu Pro Arg Ala Pro Pro Leu Gln Glu Leu Ile Asp Gln Tyr Asp Val
                 85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
                115                 120                 125

Val Gln Met Glu Gly Lys Pro Lys Cys Cys Phe Lys Phe Ser Ser
    130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
    195                 200                 205

Lys Thr Val Leu Gln Asn Trp Leu Lys Gln Pro Glu Ser Asn Leu Gly
210                 215                 220

Ile Glu Ile Lys Ala Phe Asp Glu Thr Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
                275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
    370                 375

<210> SEQ ID NO 35
<211> LENGTH: 375
<212> TYPE: PRT
<213> ORGANISM: Meleagris gallopavo
```

```
<400> SEQUENCE: 35

Met Gln Ile Leu Ala Val Tyr Val Tyr Ile Tyr Leu Phe Met Gln Ile
  1               5                  10                  15

Leu Val His Pro Val Ala Leu Asp Gly Ser Ser Gln Pro Thr Glu Asn
             20                  25                  30

Ala Glu Lys Asp Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
     50                  55                  60

Arg Leu Glu Gln Ala Pro Asn Ile Ser Arg Asp Val Ile Lys Gln Leu
 65                  70                  75                  80

Leu Pro Arg Ala Pro Pro Leu Gln Glu Leu Ile Asp Gln Tyr Asp Val
                 85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Val Gln Met Glu Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Phe Asp Glu Asn Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
370                 375

<210> SEQ ID NO 36
<211> LENGTH: 374
<212> TYPE: PRT
<213> ORGANISM: Danio rerio
```

-continued

```
<400> SEQUENCE: 36

Met His Phe Thr Gln Val Leu Ile Ser Leu Ser Val Leu Ile Ala Cys
  1               5                  10                  15

Gly Pro Val Gly Tyr Gly Asp Ile Thr Ala His Gln Gln Pro Ser Thr
             20                  25                  30

Ala Thr Glu Glu Ser Glu Leu Cys Ser Thr Cys Glu Phe Arg Gln His
         35                  40                  45

Ser Lys Leu Met Arg Leu His Ala Ile Lys Ser Gln Ile Leu Ser Lys
 50                  55                  60

Leu Arg Leu Lys Gln Ala Pro Asn Ile Ser Arg Asp Val Val Lys Gln
 65                  70                  75                  80

Leu Leu Pro Arg Ala Pro Pro Leu Gln Gln Leu Leu Asp Gln Tyr Asp
                 85                  90                  95

Val Leu Gly Asp Asp Ser Lys Asp Gly Ala Val Glu Glu Asp Asp Glu
            100                 105                 110

His Ala Thr Thr Glu Thr Ile Met Thr Met Ala Thr Glu Pro Asp Pro
            115                 120                 125

Ile Val Gln Val Asp Arg Lys Pro Lys Cys Cys Phe Phe Ser Phe Ser
130                 135                 140

Pro Lys Ile Gln Ala Asn Arg Ile Val Arg Ala Gln Leu Trp Val His
145                 150                 155                 160

Leu Arg Pro Ala Glu Glu Ala Thr Thr Val Phe Leu Gln Ile Ser Arg
                165                 170                 175

Leu Met Pro Val Lys Asp Gly Gly Arg His Arg Ile Arg Ser Leu Lys
            180                 185                 190

Ile Asp Val Asn Ala Gly Val Thr Ser Trp Gln Ser Ile Asp Val Lys
            195                 200                 205

Gln Val Leu Thr Val Trp Leu Lys Gln Pro Glu Thr Asn Arg Gly Ile
210                 215                 220

Glu Ile Asn Ala Tyr Asp Ala Lys Gly Asn Asp Leu Ala Val Thr Ser
225                 230                 235                 240

Thr Glu Thr Gly Glu Asp Gly Leu Leu Pro Phe Met Glu Val Lys Ile
                245                 250                 255

Ser Glu Gly Pro Lys Arg Ile Arg Arg Asp Ser Gly Leu Asp Cys Asp
            260                 265                 270

Glu Asn Ser Ser Glu Ser Arg Cys Cys Arg Tyr Pro Leu Thr Val Asp
            275                 280                 285

Phe Glu Asp Phe Gly Trp Asp Trp Ile Ile Ala Pro Lys Arg Tyr Lys
290                 295                 300

Ala Asn Tyr Cys Ser Gly Glu Cys Asp Tyr Met Tyr Leu Gln Lys Tyr
305                 310                 315                 320

Pro His Thr His Leu Val Asn Lys Ala Ser Pro Arg Gly Thr Ala Gly
                325                 330                 335

Pro Cys Cys Thr Pro Thr Lys Met Ser Pro Ile Asn Met Leu Tyr Phe
            340                 345                 350

Asn Gly Lys Glu Gln Ile Ile Tyr Gly Lys Ile Pro Ser Met Val Val
            355                 360                 365

Asp Arg Cys Gly Cys Ser
370

<210> SEQ ID NO 37
<211> LENGTH: 6
<212> TYPE: PRT
<213> ORGANISM: Artificial Sequence
```

-continued

```
<220> FEATURE:
<223> OTHER INFORMATION: Description of Artificial Sequence: myostatin
      peptide

<400> SEQUENCE: 37

Lys Arg Ser Arg Arg Asp
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: myostatin
      peptide

<400> SEQUENCE: 38

Lys Glu Asn Val Glu Lys Glu
  1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: mystatin
      peptide

<400> SEQUENCE: 39

Ser Leu Lys Asp Asp Asp
  1               5
```